(12) United States Patent
Endo et al.

(10) Patent No.: US 7,452,983 B2
(45) Date of Patent: Nov. 18, 2008

(54) PROTEIN WHICH BINDS TO AKT2

(75) Inventors: Yuki Endo, Tsukuba (JP); Hideki Endoh, Tsukuba (JP); Yoshitaka Ueda, Tsukuba (JP); Miyuki Kato, Tsukuba (JP); Kazunori Inabe, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 164 days.

(21) Appl. No.: 10/537,767

(22) PCT Filed: Dec. 4, 2003

(86) PCT No.: PCT/JP03/15546

§ 371 (c)(1),
(2), (4) Date: Jun. 6, 2005

(87) PCT Pub. No.: WO2004/050869

PCT Pub. Date: Jun. 17, 2004

(65) Prior Publication Data

US 2006/0211041 A1  Sep. 21, 2006

(30) Foreign Application Priority Data

Dec. 5, 2002 (JP) .............................. 2002-354155
Aug. 8, 2003 (JP) .............................. 2003-206952

(51) Int. Cl.
*C07H 21/04* (2006.01)
*C12N 15/63* (2006.01)
*C12N 15/85* (2006.01)
*C12N 15/86* (2006.01)
*C12N 1/21* (2006.01)
*C12N 5/14* (2006.01)
*C12N 1/20* (2006.01)
*C07K 14/00* (2006.01)

(52) U.S. Cl. .................. 536/23.1; 536/23.5; 435/320.1; 435/252.3; 435/41; 435/325; 435/410; 530/350

(58) Field of Classification Search ....................... None
See application file for complete search history.

(56) References Cited

U.S. PATENT DOCUMENTS

2003/0181366 A1   9/2003   Luo et al.
2003/0219741 A1   11/2003  Isogai et al.

FOREIGN PATENT DOCUMENTS

EP   1 293 569 A2   3/2003
JP   2003-88388 A   3/2003

OTHER PUBLICATIONS

Whiteman et al., Trends in Endocrinology & Metabolism, 2002, 13(10): 444-451.*
Ngo et al., in The Protein Folding Problem and Tertiary Structure Prediction, 1994, Merz et al. (ed.), Birkhauser, Boston, MA, pp. 433 and 492-495.*
Yasuhiro Mitsuuchi, et al., "Identification of a chromosome 3p14.3-21.1 gene, *APPL*, encoding an adaptor molecule that interacts with the oncoprotein-serine/threonine kinase AKT2", Oncogebe, 1999, pp. 4891-4898, vol. 18.

* cited by examiner

*Primary Examiner*—Delia M. Ramirez
*Assistant Examiner*—Jae W Lee
(74) *Attorney, Agent, or Firm*—Sughrue Mion, PLLC

(57) ABSTRACT

A novel polypeptide, a polynucleotide, an expression vector, a cell transfected with the expression vector, a method for screening an insulin resistance improving agent and a carbohydrate metabolism improving agent, and a method for producing a pharmaceutical composition are provided. The polypeptide is useful in screening an insulin resistance improving agent and a carbohydrate metabolism improving agent. When the polypeptide is overexpressed in a fat cell, the activity of Akt2 is reduced. Fat cells express the polypeptide. The polynucleotide encodes the polypeptide. The expression vector includes the polynucleotide. The screening method uses the polypeptide to screen for an insulin resistance improving agent and a carbohydrate metabolism improving agent. The production method uses the substance obtained by the screening method as the active ingredient of the pharmaceutical composition. The pharmaceutical composition is useful for insulin resistance improvement and carbohydrate metabolism improvement.

5 Claims, 3 Drawing Sheets

FIG. 2 (1)
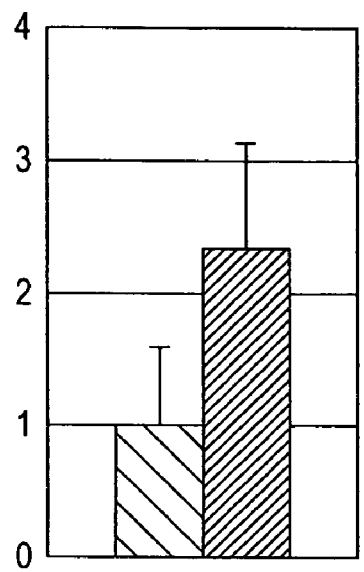
FIG. 2 (2)
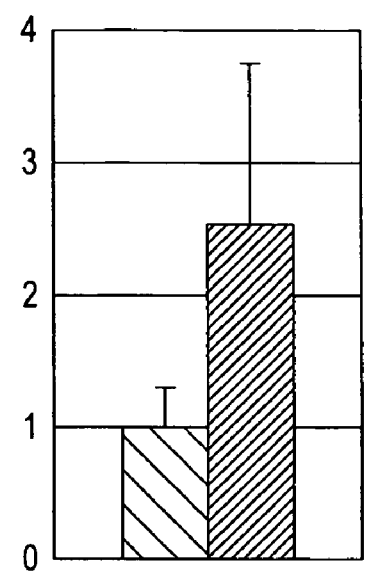
FIG. 2 (3)
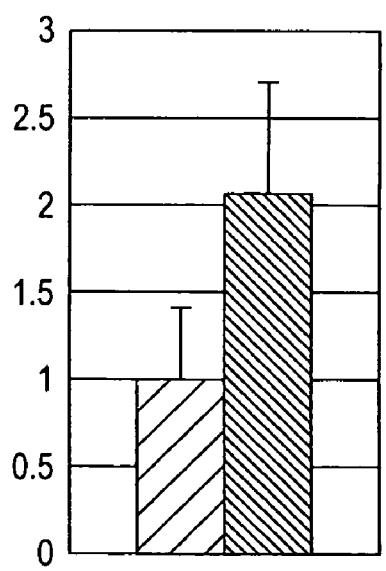
FIG. 2 (4)
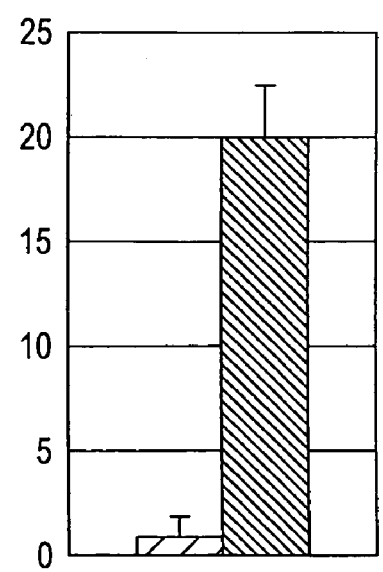

PROTEIN WHICH BINDS TO AKT2

TECHNICAL FIELD

The present invention relates to a novel polypeptide which binds to Akt2, and a novel polynucleotide coding for said polypeptide, a vector comprising said polynucleotide, a transformed cell comprising said vector and a method for screening a substance which inhibits binding of the aforementioned polypeptide with Akt2.

BACKGROUND OF THE INVENTION

Insulin is secreted from β cells of the pancreatic islets of Langerhans and reduces blood sugar level by mainly acting upon muscle, the liver and adipose and thereby incorporating blood sugar into cells to effect its storage and consumption. Diabetes mellitus is induced by insufficient action of this insulin, and two types are present in its patients, namely type 1 having a disorder of the production or secretion of insulin and type 2 having a difficulty in accelerating carbohydrate metabolism by insulin. The blood sugar level in both of these patients becomes higher than that in healthy person, but while insulin in blood is absolutely insufficient in type 1, insulin resistance occurs in type 2 in which incorporation or consumption of blood sugar by cells is not accelerated in spite of the presence of insulin. The type 2 diabetes mellitus is a so-called lifestyle-related disease which is generated due to overeating, lack of exercise, stress and the like causes in addition to the hereditary predisposition. Nowadays, patients of this type 2 diabetes mellitus are rapidly increasing in advanced nations accompanied by the increase of ingestion calories, and this type occupies 95% of diabetes mellitus patients in Japan. Accordingly, necessity is increasing not only for a simple hypoglycemic drug as a therapeutic agent for diabetes mellitus but also on a study which aims at treating type 2 diabetes mellitus for the purpose of accelerating carbohydrate metabolism through the improvement of insulin resistance.

At present, insulin injections are prescribed for the treatment of type 1 diabetes mellitus patients. On the other hand, in addition to the insulin injections, sulfonylurea hypoglycemic agents (SU preparations) which prompts secretion of insulin by acting upon β cells of the pancreas and biguanide hypoglycemic agents which have actions to increase sugar usage and inhibit gluconeogenesis by anaerobic glycolysis action and to inhibit intestinal absorption of sugar, as well as α-glucosidase inhibitors which delay digestion and absorption of saccharides, are known as the hypoglycemic agents prescribed for type 2 patients. Though these indirectly improve insulin resistance, thiazolidine derivatives have been used in recent years as agents which directly improve insulin resistance. Its action is to accelerate incorporation of glucose into cells and use of glucose in cells. It is shown that the thiazolidine derivatives act as an agonist of peroxisome proliferator responding activated receptor gamma (PPARγ) (cf. Non-patent reference 1). However, it is known that the thiazolidinediones not only improve insulin resistance but also have a side effect to induce edema (cf. Non-patent reference 2, Non-patent reference 3). Since this induction of edema is a serious side effect which results in cardiac hypertrophy, more useful target molecule for drug development than the PPARγ is in demand for the improvement of insulin resistance.

The signal of insulin action is transferred into cells via an insulin receptor on the cell membrane. Two pathways of the first and second are present in this insulin action pathway (cf. Non-patent reference 4). In the first pathway, the signal is transferred in order from the activated insulin receptor to Akt1 (PKBα) or Akt2 (PKBβ), or PKCγ or PKCζ, via IRS-1, IRS-2, PI 3 kinase and PDK 1, and incorporation of sugar from the extracellular moiety is accelerated as the result by translocating a glucose transporter GLUT 4 existing inside the cell onto the cell membrane (cf. Non-patent reference 5). On the other hand, in the second pathway, the signal is transferred from the insulin receptor to CrK II, C3G and TC 10 in that order via c-Cbl and CAP, and incorporation of sugar by GLUT 4 is accelerated as the result (cf. Non-patent reference 6). However, there are portions still unclear regarding details of these insulin signal transduction pathways, and it is not clear particularly about the mechanism which finally mediates acceleration of sugar incorporation of cells by these signals via the glucose transporter.

Akt2 is present in the aforementioned insulin signal first pathway and activated by undergoing phosphorylation by insulin stimulation via PDK 1. The activated Akt2 transfers the signal as a kinase by phosphorylating a protein as its substrate. It has been reported that a homo-knockout mouse in which a gene coding for the Akt2 protein was artificially deleted shows a type 2 diabetes-like phenotype due to reduced insulin sensitivity mainly in muscle and the liver. Based on these facts, it has been considered that Akt2 is a signal mediating factor which functions in incorporating sugar into cells in response to the insulin signal, and its functional inhibition induces insulin resistance by partial interception of the insulin signal transduction (cf. Non-patent reference 7).

(Non-patent Reference 1)
"*The Journal of Biological Chemistry*", (USA), 1995, vol. 270, pp. 12953-12956

(Non-patent Reference 2)
"*Diabetes Frontier*", (USA), 1999, vol. 10, pp. 811-818

(Non-patent Reference 3)
"*Diabetes Frontier*", (USA), 1999, vol. 10, pp. 819-824

(Non-patent Reference 4)
"*The Journal of Clinical Investigation*", (USA), 2000, vol. 106, no. 2, pp. 165-169

(Non-patent Reference 5)
"*The Journal of Biological Chemistry*", (USA), 1999, vol. 274, no. 4, pp. 1865-1868

(Non-patent Reference 6)
"*Nature*", (England), 2001, vol. 410, no. 6831, pp. 944-948

(Non-patent Reference 7)
"*Science*", (USA), 2002, vol. 292, no. 2, pp. 1728-1731

DISCLOSURE OF THE INVENTION

Based on the aforementioned information, the present inventors considered that insulin resistance may be improved when function of Akt2 can be increased. It was considered that this object may be achieved by increasing activity of the Akt2 itself, or by regulating the activity of a newly identified intracellular factor which binds to Akt2 and thereby controls its activity. However, since Akt2 is a kinase, it is difficult to regulate its enzyme activity toward increasing direction by a drug. Accordingly, a protein which binds to Akt2 was identified by a yeast two hybrid system. As a result, it was successful in cloning a mouse derived cDNA of a novel nucleotide sequence coding for a protein AKBP 2 (Akt2 Binding Protein 2) which binds to Akt2. Also, since expressed amount of this protein was considerably increased in muscle and adipose of model mice of diabetes mellitus in comparison with normal individuals, it was found that this protein is a causal factor of the morbid state of diabetes mellitus. In addition, by succeeding in cloning a human orthologue human AKBP 2 gene, it was found that said gene is expressed in fat cells as an insulin response tissue and that human AKBP 2 also binds to Akt2 as the case of mouse AKBP 2. In addition to this, by detecting that kinase activity of Akt2 is reduced by overexpression of mouse AKBP 2, it was found that insulin resistance is induced by the interception of insulin signal by AKBP 2, that is, insulin resistance is improved by-inhibiting binding of AKBP 2 with Akt2. Accordingly, a screening system for an insulin resistance improving agent and/or a carbohydrate metabolism improving agent was constructed making use of the interaction of AKBP 2 with Akt2.

As these results, the present invention was accomplished by providing a novel polypeptide useful in screening an insulin resistance improving agent and/or a carbohydrate metabolism improving agent, a polynucleotide coding for the aforementioned polypeptide, an expression vector comprising the aforementioned polynucleotide, a cell transformed with the aforementioned expression vector, a method for screening an insulin resistance improving agent and/or a carbohydrate metabolism improving agent, and a method for producing a pharmaceutical composition for insulin resistance improvement and/or carbohydrate metabolism improvement.

That is, the present invention relates to

[1] a polypeptide which comprises the amino acid sequence represented by SEQ ID NO:2 or SEQ ID NO:4, or an amino acid sequence in which from 1 to 10 amino acids are deleted, substituted and/or inserted in the amino acid sequence represented by SEQ ID NO:2 or SEQ ID NO:4, and which binds to Akt2,

[2] a polypeptide consisting of the amino acid sequence represented by SEQ ID NO:2 or SEQ ID NO:4,

[3] a polynucleotide coding for the polypeptide described in [1] or [2],

[4] an expression vector comprising the polynucleotide described in [3],

[5] a cell transformed with the expression vector described in [4],

[6] a method for screening a substance which inhibits binding of a polypeptide described in claim 1 or claim 2 or a polypeptide consisting of an amino acid sequence having a homology of 90% or more with the amino acid sequence represented by SEQ ID NO:2 or SEQ ID NO:4 and which binds to Akt2, with Akt2, which comprises allowing (1) the aforementioned polypeptide or a cell expressing the aforementioned polypeptide, to contact (2) a substance to be tested, measuring binding of said polypeptide with Akt2, and selecting a substance which inhibits the aforementioned binding,

[7] the screening method described in [6], wherein the binding inhibiting substance is an insulin resistance improving agent and/or a carbohydrate metabolism improving agent,

[8] the screening method described in [6] or [7], wherein the step of measuring binding of (1) the polypeptide described in [1] or [2] or a polypeptide consisting of an amino acid sequence having a homology of 90% or more with the amino acid sequence represented by SEQ ID NO:2 or SEQ ID NO:4, and which binds to Akt2, to (2) Akt2 is a step of measuring a change in Akt2 based on the change in the aforementioned binding, and

[9] a method for producing a pharmaceutical composition for insulin resistance improvement and/or carbohydrate metabolism improvement, which comprises carrying out screening using the screening method described in [6] to [8], and preparing a pharmaceutical preparation.

Virtually nothing is known about the sequences identical to the polypeptides and polynucleotides of the present invention described in SEQ ID NOs:1 to 4. Though sequences having homology with the polynucleotides of the present invention have been reported in a sequence data base GenBank as accession numbers AX714043, BC042155 and BC049110 after the priority date of this application, this is merely a disclosure of sequences and there is no description on their illustrative use. Also, a sequence data base GenPept carries, as an accession number AK056090, a polypeptide consisting of an amino acid sequence in which 68 amino acids of the amino acid sequence represented by SEQ ID NO:4 as one of the polypeptides of the present invention are deleted, and as an accession number AK019105, a polypeptide consisting of an amino acid sequence in which 228 amino acids of the amino acid sequence represented by SEQ ID NO:2 as one of the polypeptides of the present invention are deleted and 13 amino acids of the same are substituted. However, there is no information that these polypeptides were actually prepared, and there is no information on how to prepare them. In addition, illustrative use of said polypeptides is not described either. The present inventors have found the polypeptides and polynucleotides of the present invention for the first time and revealed for the first time that overexpression of the protein and increase of its binding to Akt2 are causal factors of the morbid state of diabetes mellitus. In addition, the screening methods of the present invention by making use of the binding of the polypeptide of the present invention with Akt2 are methods provided for the first time by the present inventors.

BRIEF DESCRIPTION OF THE DRAWINGS

FIG. 2 (1) is a graph showing comparison of AKBP2 expression level in adipose of normal mice C57BL/6J loaded with a normal feed or a high fat feed. Vertical axis of the drawing shows relative expression level in mouse fat. The white bar shows when the normal feed was loaded, and the black bar when the high fat feed was loaded.

Figure 1:
FIG. 1 is a graph showing expression of AKBP2 in cultured cells. Lanes 1 and 3 indicate molecular weight markers, and lane 2 an empty vector and lane 4 a case of introducing pcDNA-AKBP2.

The (2) is a graph showing comparison of AKBP2 expression level in muscle of the normal mice C57BL/6J loaded with a normal feed or a high fat feed. Vertical axis of the drawing shows relative expression level in mouse muscle. The white bar shows when the normal feed was loaded, and the black bar when the high fat feed was loaded.

The (3) is a graph showing comparison of AKBP2 expression level in adipose of the normal mice C57BL/6J and diabetes mellitus model mice KKA$^y$/Ta. Vertical axis of the drawing shows relative expression level in mouse adipose. The white bar shows a result of the normal mice C57BL/6J, and the lined bar that of the diabetes mellitus model mice KKA$^y$/Ta.

The (4) is a graph showing comparison of AKBP2 expression level in muscles of the normal mice C57BL/6J and the diabetes mellitus model mice KKA$^y$/Ta. Vertical axis of the drawing shows relative expression level in mouse muscle.

The white bar shows a result of the normal mice C57BL/6J, and the lined bar that of the diabetes mellitus model mice KKA$^y$/Ta.

Expression level in normal feed C57BL/6J is shown as 1 in the comparison in (1) and (2), and expression level in C57BL/6J is shown as 1 in the comparison in (3) and (4), respectively.

Figure 3:
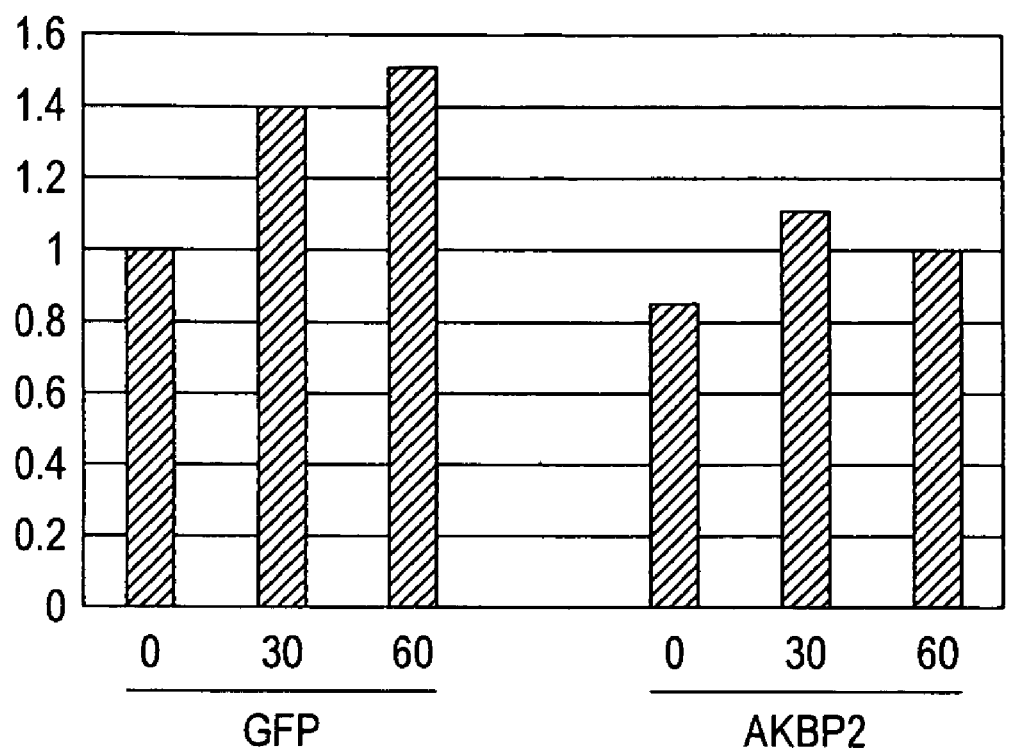

FIG. 3 is a graph showing influence of mouse AKBP2 overexpression in NIH3T3 L1 fat cells upon Akt2 enzyme activity. Vertical axis of the drawing shows relative activity, and the value of the enzyme activity in the cells infected with a control virus under the condition of no insulin stimulus is shown as 1. Horizontal axis of the drawing shows insulin stimulation period (minute).

BEST MODE FOR CARRYING OUT THE INVENTION

The following describes the present invention in detail.
<Polypeptide of the Invention>
Included in the polypeptide of the present invention are (1) a polypeptide consisting of the amino acid sequence represented by SEQ ID NO:2 or SEQ ID NO:4; and (2) i) a polypeptide which comprises the amino acid sequence represented by SEQ ID NO:2 or SEQ ID NO:4 and which binds to Akt2, or ii) a polypeptide which comprises an amino acid sequence in which from 1 to 10 (preferably from 1 to 7, more preferably from 1 to 5, further preferably from 1 to 3) amino acids are deleted, substituted and/or inserted in the amino acid sequence represented by SEQ ID NO:2 or SEQ ID NO:4 and which binds to Akt2 (to be referred to as functionally equivalent variant hereinafter).

Those which reduce kinase activity of Akt2 by binding to Akt2 are particularly desirable as the polypeptides of the present invention.

Also, the polypeptides of the present invention are not particularly limited to the human and mouse derived polypeptides as long as they come under either of the aforementioned (1) and (2), and those which are derived from other vertebrates (e.g., rat, rabbit, horse, sheep, dog, monkey, cat, bear, pig, domestic fowl and the like) are also included therein. In addition, they are not limited to natural polypeptides and artificially produced mutants are also included therein, as long as they come under either of the aforementioned (1) and (2).

The term "binds to Akt2" means that a polypeptide binds to Akt2 (preferably human Akt2, more preferably the polypeptide encoded by the GenBank accession number M95936), and whether or not it "binds" may be verified by the following methods.

A partial or the entire length of a polypeptide to be examined for whether or not it binds, or a partial or the entire length of a polypeptide to be examined fused with a tag (e.g., GST, Flag, His or the like), is expressed in a cell. As the aforementioned cell, a cell which responds to insulin is desirable, and more illustratively, fat cell, hepatocyte or a skeletal muscle-derived cell is desirable. Akt2 protein and a protein which binds thereto may be concentrated from the aforementioned cell by immunoprecipitation using an anti-Akt2 antibody. Whether or not the polypeptide to be examined binds to Akt2 may be verified by separating concentrated solution of the thus obtained Akt2 and its binding protein by polyacrylamide gel electrophoresis through a conventionally known method and then carrying out western blotting using an antibody. Regarding the antibody to be used in this case, an antibody for the polypeptide to be examined or a polypeptide to be examined prepared based on its partial sequence, or an antibody which recognizes the aforementioned tag may be used.

In addition, binding of the polypeptide to be examined with a polypeptide can also be detected by combining a western blotting similar to the aforementioned one with an in vitro pull down method (H. Matsushime et al., Jikken Kogaku (Experimental Engineering), Vol. 113, No. 6, p. 528, 1994) which uses an extract of cells in which the polypeptide to be examined is expressed, or a mixed solution of proteins prepared by in vitro transcription and translation, and Akt2 protein purified by attaching a tag (e.g., GST or the like). Preferably, the binding may be detected using a mixed solution of proteins prepared by directly carrying out in vitro transcription and translation of the protein to be examined as shown in Example 6, from a plasmid for use in the expression of the protein to be examined (e.g., the plasmid for AKBP2 protein expression prepared in Example 1(5)) using an in vitro translation kit (e.g., TNT Kit (Promega)). More preferably, binding of the polypeptide to be examined to Akt2 may be detected by the method described in Example 6. The term "to reduce kinase activity of Akt2" means that the kinase activity possessed by Akt2 is reduced through the binding of the polypeptide to be examined to Akt2. Whether or not the "kinase activity is reduced" may be verified by the following method.

It is known that the kinase activity of Akt2 is accelerated when the 473rd serine (Ser 473) or the 308th threonine (Thr 308) in the molecule is phosphorylated (*Biochem. J.*, 1998, 335 (1-13)). Making use of this, the presence or absence of Akt2 activity may be detected by detecting phosphorylated condition of the Ser 473 or Thr 308 of Akt2 by a western blotting which uses an antibody capable of specifically reacting with these phosphorylated residues (e.g. anti-phosphoSer antibody or the like). More illustratively, phosphorylation of Akt2, namely the presence or absence of Akt2 activity, may be detected by lysing cells (a cell which responds to insulin is desirable, and more illustratively, fat cell, hepatocyte or a skeletal muscle-derived cell is desirable) in which a part or the entire length of the polypeptide to be examined is expressed, and using this as the sample, carrying out western blotting, spot western blotting or the like method which uses the anti-phosphoSer antibody. Preferably, this may be detected by the method of Example 7. When reduction of the phosphorylation of Akt2 (namely activation of Akt2) was observed in this detection system by the use of a sample obtained from a cell in which the polypeptide to be examined was expressed, in comparison with a cell in which the polypeptide to be examined was not expressed, it may be judged that the polypeptide to be examined "reduces kinase activity of Akt2".

In addition, whether or not it "reduces kinase activity of Akt2" can also be verified by an in vitro kinase assay method in which uptake of radioactive phosphoric acid based on a substrate is measured when a histone H2B, a GSK-3 fusion protein or the like is used as the substrate of Akt2 and allowed to react with an immune precipitate of Akt2. Illustratively, Akt2 protein may be concentrated from an extract of cells (a cell which respond to insulin is desirable, and more illustratively, fat cell, hepatocyte or a skeletal muscle-derived cell is desirable) in which a part or the entire length of the polypeptide to be examined is expressed, by immunoprecipitation using an anti-Akt2 antibody. By mixing a substrate of Akt2, such as GST-crosstide (GST fusion protein of GSK3-beta as a physiological substrate of Akt), with concentrated Akt2 protein, kinase activity of Akt2 may be measured-and determined using phosphorylation of the substrate as the index. Preferably, this may be measured by the method described in Example 7. When reduction of the phosphorylation of the substrate was observed in this measuring system by the use of a sample obtained from a cell in which the polypeptide to be examined was expressed, in comparison with a cell in which the polypeptide to be examined was not expressed, it may be judged that the polypeptide to be examined "reduces kinase activity of Akt2".

<Polynucleotide of the Invention>

The polynucleotide of the present invention may be derived from any species, as long as it encodes the polypeptide of the present invention, namely a polypeptide represented by the amino acid sequence described in SEQ ID NO:2 or SEQ ID NO:4, or a functionally equivalent variant thereof. Preferred is a polynucleotide consisting of a nucleotide sequence coding for the amino acid sequence described in SEQ ID NO:2 or SEQ ID NO:4, and further preferred is the nucleotide sequence described in SEQ ID NO:1 or SEQ ID NO:3. In this connection, both of DNA and RNA are included in the "polynucleotide" according to this description.

All kinds of mutants may be included in the polynucleotide of the present invention, as long as they encode the polypeptide of the present invention. More illustratively, it can include allele mutants which are present in the natural world, mutants which are not present in the natural world, and mutants which have deletion, substitution, addition and insertion. The aforementioned mutation sometimes occur by natural mutation, but it can also be effected by carrying out artificial modification. All mutant genes coding for the aforementioned polypeptide of the present invention are included in the present invention, regardless of the cause and means of mutation of the aforementioned polypeptide. As the aforementioned artificial means leading to the preparation of mutants, for example, in addition to genetic engineering techniques such as base-specific substitution method (*Methods in Enzymology,* (1987), 154, 350, 367-382) and the like, chemical synthesis means such as phosphotriester method, phosphoamidide method and the like (*Science*, 150, 178, 1968) may be cited. By their combination, it is possible to obtain a DNA accompanied by the desired base substitution. Alternatively, it is possible to generate a substitution in a nonspecific base in the DNA molecule by the repetition of PCR or by allowing manganese ion or the like to be present in the reaction solution.

The polynucleotide and polypeptide of the present invention may be easily produced and obtained by general genetic-engineering techniques based on the sequence information disclosed by the present invention.

The polynucleotide coding for the polypeptide of the present invention may be prepared for example in the following manner, but it may be prepared not only by this method but also by conventionally known operations "Molecular Cloning, Sambrook, J. et al., Cold Spring Harbor Laboratory Press, 1989" and the like.

For example, (1) a method which uses PCR, (2) general genetic engineering techniques (namely a method in which a transformant comprising desired amino acids is selected from transformants transformed with a cDNA library), (3) a chemical synthesis method or the like may be cited. Each production method may be carried out in the same manner as described in WO 01/34785.

By the method which uses PCR, the polynucleotide described in this description may be produced for example by the procedure described in the "Mode for Carrying Out the Invention", 1) Production method of protein gene, a) First production method, of the aforementioned patent reference. Regarding the "human cell or tissue having the ability to produce the protein of the present invention" in said description, adopose cells can for example be cited. Total mRNA is extracted from human or murine adipose cells. Next, a first-strand cDNA may be synthesized by subjecting this mRNA-to a reverse transcriptase reaction in the presence of random primers or oligo dT primers. The polynucleotide of the present invention or a part thereof may be obtained by subjecting the thus obtained first-strand cDNA to polymerase chain reaction (PCR) using two kinds of primers interposing a partial region of the gene of interest. More illustratively, the polynucleotide of the present invention may be produced for example by the methods described in Example 1 and Example 4.

By the method which uses general genetic engineering techniques, the polynucleotide coding for the polypeptide of the present invention may be produced for example by the procedure described in the "Mode for Carrying Out the Invention", 1) Production method of protein gene, b) Second production method, of the aforementioned patent reference.

By the method which uses chemical synthesis, the polynucleotide coding for the polypeptide of the present invention may be produced for example by the procedure described in the "Mode for Carrying Out the Invention", 1) Production method of protein gene, c) Third production method, d) Fourth production method, of the aforementioned patent reference.

By making use of partial or entire nucleotide sequence of the thus obtained polynucleotide of the present invention, expression level of the polynucleotide of the present invention in each individual or various tissues may be specifically detected.

Examples of such a detection method include RT-PCR (reverse transcribed-polymerase chain reaction), northern blotting analysis, in situ hybridization and the like methods.

<Production Methods of the Expression Vector, Cell and Polypeptide of the Invention>

Also included in the present invention is a method for producing the polypeptide of the present invention, which is characterized in that the transformed cell of the present invention is cultured.

The polynucleotide coding for the polypeptide of the present invention, obtained in the aforementioned manner, may be used for expressing the polypeptide of the present invention in a test tube or in a test cell by connecting it to the downstream of an appropriate promoter, by conventionally known methods described in "Molecular Cloning, Sambrook, J. et al., Cold Spring Harbor Laboratory Press, 1989" and the like.

Illustratively, by adding a polynucleotide containing a specified promoter sequence to upstream of the initiation codon for the polypeptide of the present invention obtained in the aforementioned manner, it is possible to effect expression of the polypeptide of the present invention by cell-free system transcription and translation of the gene using this as the template.

Alternatively, expression of the polypeptide of the present invention in a cell becomes possible when the aforementioned polynucleotide coding for the polypeptide of the present invention is integrated into an appropriate vector plasmid and introduced in the form of plasmid into a host cell. Alternatively, a cell in which such a construction is integrated into chromosomal DNA may be prepared and used. More illustratively, an isolated fragment containing a polynucleotide can transform host cells of eukaryotes and prokaryotes by again integrating into an appropriate vector plasmid. Furthermore, it is possible to effect expression of the polypeptide of the present invention in respective host cells by introducing an appropriate promoter and a sequence concerned in the gene expression into these vectors. The host cell is not particularly limited, as long as it can detect expression of the polypeptide of the present invention at the mRNA level or protein level. It is most desirable to use a fat-derived cell or muscle-derived cell as the host cell, in which endogenous Akt2 is abundantly present.

The method for expressing a gene by transforming a host cell may be carried out, for example, by the method described in the "Mode for Carrying Out the Invention", 2) Method for producing the vector of the present invention, the host cell of the present invention and the recombinant protein of the present invention, of the aforementioned patent reference. The expression vector is not particularly limited, as long as it contains a desired polynucleotide. An example thereof is an expression vector obtained by inserting the desired polynucleotide into a conventionally known expression vector optionally selected in response to the host cell to be used. The cell of the present invention may be obtained, for example, by transfecting a desired host cell with the aforementioned expression vector. More illustratively, an expression vector for a desired protein may be obtained, for example, by integrating a desired polynucleotide into an expression vector for mammal cell, pcDNA3.1, as described in Example 2, and the transformed cell of the present invention may be produced by incorporating said expression vector into the 293 cell using the calcium phosphate method.

The desired transformed cell obtained in the above may be cultured in accordance with a general method, and the desired protein is produced by said culturing. Regarding the medium to be used in said culturing, various generally used kinds may be optionally selected in response to the employed host cell. For example, in the case of the aforementioned 293 cell, Dulbecco's modified Eagle's minimum essential medium (DMEM) supplemented with serum component (e.g., fetal bovine serum (FBS) or the like), to which G418 was further added, may be used. As the transformed cell of the present invention, a cell expressing the polypeptide of the present invention is desirable.

By culturing the cell of the present invention, the polypeptide of the present invention produced in the cell may be detected, determined and also purified. For example, it is possible to detect and purify the polypeptide of the present invention by western blotting or immunoprecipitation using an antibody which binds to the polypeptide of the present invention. Alternatively, by expressing the polypeptide of the present invention as a fusion protein with appropriate tag protein (e.g.,. glutathione-S-transferase (GST), protein A, β-galactosidase, maltose-binding protein (MBP) or the like), the polypeptide of the present invention may be detected by western blotting or immunoprecipitation using an antibody specific for such a tag proteins and purified making use of the tag protein. More illustratively, it may be purified making use of a tag protein in the following manner.

The polypeptide of the present invention (e.g., the polypeptide represented by SEQ ID NO:2 or SEQ ID NO:4) may be obtained by integrating the polynucleotide of the present invention (e.g., the polynucleotide represented by SEQ ID NO:1 or SEQ ID NO:3) for example into a His tag fusing vector, more illustratively for example into the pcDNA3.1/V5-His-TOPO (Invitrogen) or the like described in Example 1, to effect its expression in a cultured cell, purifying it using His tag, and then removing the tag moiety. For example, the mouse or human AKBP2 expression plasmid prepared in Example 1 or Example 5 using pcDNA3.1/V5-His-TOPO is designed in such a manner that V5 and His tag are added to the C-terminus of AKBP2 in both cases. Accordingly, the AKBP2 protein may be purified from the AKBP2-expressed cultured cells shown in Example 2 or Example 5, using the His tag. Illustratively, the AKBP2 protein fused with His tag may be isolated from an extract of disrupted cells by binding it to $Ni^{2+}$-NTA-Agarose (Funakoshi) and centrifuging the product, in accordance with known methods (Jikken Igaku (Experimental Medicine) Supplement, Tanpakushitsu-no Bunshikan Sogosayo Jikkenhou (Experimentation on Intermolecular Interaction of Protein), page 32, 1996, Nakahara et al.). More illustratively, cells expressing the polypeptide of the present invention cultured using a culture flasks (e.g., Petri dish of 10 cm in diameter) are scratched off after adding an appropriate volume (e.g., 1 ml) of a buffer solution and then centrifuged at 1,5000 rpm for 5 minutes, and an appropriate amount (e.g., 50 μM) of $Ni^{2+}$-NTA-Agarose substituted by an appropriate buffer solution is added to the thus separated supernatant and thoroughly mixed (e.g., 10 minutes or more of stirring using a rotator). Next, the supernatant is separated and removed by centrifugation (e.g., 2,000 rpm for 2 minutes) and again centrifuged by adding an appropriate amount (e.g., 0.5 ml) of a buffer solution adjusted to pH 6.8, thereby effecting washing. After repeating this 3 times, an appropriate amount (e.g., 50 μl) of 100 mM EDTA is added, the mixture is allowed to stand for 10 minutes and then the supernatant is recovered, thereby enabling purification of the released polypeptide of the present invention. As the aforementioned buffer solution, a buffer solution B (8 M urea, 0.1 M $Na_2HPO_4$, 0.1 M $NaH_2PO_4$, 0.01 M Tris-HCl pH 8.0) can for example be used. The His tag in the purified protein molecule may be removed from the molecule, for example, by designing in such a manner that His tag is fused to the N-terminal side and using TAGZyme System (Qiagen).

Alternatively, as occasion demands, it may be purified by a method which does not use a tag protein, for example, by various separation operations making use of the physical properties and chemical properties of the protein consisting of the polypeptide of the present invention. Illustratively, use of ultrafiltration, centrifugation, gel filtration, adsorption chromatography, ion exchange chromatography, affinity chromatography and high performance liquid chromatography may be exemplified.

The polypeptide of the present invention may be produced by general chemical synthesis in accordance-with the amino acid sequence information shown in SEQ ID NO:2 or SEQ ID NO:4. Illustratively, liquid phase and solid phase peptide synthesis methods are included. Its synthesis may be carried out by successively binding one amino acid after another, or by synthesizing a peptide fragment comprising several amino acids and the binding it. The polypeptide of the present invention obtained by these means may be purified in accordance with the aforementioned various methods.

<Inspection Method of *Diabetes Mellitus*>

By the use of a probe which hybridizes with the polynucleotide of the present invention under a stringent condition, expressed amount of a polynucleotide coding for the polypeptide of the present invention may be examined, and diagnosis of diabetes mellitus can be carried out using increase of the expressed amount (preferably the expressed amount in the fat tissue) as the index. In the inspection method of diabetes mellitus, the term "stringent condition" means a condition under which nonspecific binding does not occur, and illustratively, it means a condition in which 0.1× SSC (saline-sodium citrate buffer) solution containing 0.1% sodium lauryl sulfate (SDS) is used and the temperature is 65° C. As the probe, a DNA of at least 15 bp in chain length and having at least a part of or entire sequence (or a complementary sequence thereof) of the polynucleotide of the present invention is used.

According to the method for detecting diabetes mellitus, whether or not the subject is diabetes mellitus may be detected by allowing the aforementioned probes to contact a sample to be tested, and analyzing the bonded product of a polynucleotide coding for the polypeptide of the present invention (e.g., mRNA or cDNA derived therefrom) and the aforementioned probe by a conventionally known analyzing method (e.g., northern blotting). In addition, the expression quantity can also be analyzed by applying the aforementioned probe to a DNA tip. When the amount of the aforementioned bonded product, namely the amount of a polynucleotide coding for the polypeptide of the present invention, is increased in comparison with healthy parsons, it may be judged that the subject is diabetes mellitus.

As a method for measuring expressed level of the polynucleotide of the present invention, it is possible to employ methods in which the expressed level is measured by detecting the polypeptide of the present invention. Examples of the inspection method to be used include western blotting, immunoprecipitation, ELISA and the like methods, making use of an antibody which binds a sample to be tested to the polypeptide of the present invention, or an antibody which specifically binds to the polypeptide of the present invention. In determining the amount of the polypeptide of the present invention contained in the sample to be tested, the polypeptide of the present invention may be used as the standard amount. In addition, the polypeptide of the present invention is useful for preparing an antibody which binds to the polypeptide of the present invention. When the amount of the polypeptide of the present invention is increased in comparison with healthy parsons, it may be judged that the subject is diabetes mellitus.

<Screening Method of the Invention>

By using (1) the polypeptide of the present invention, (2) a polypeptide consisting of an amino acid sequence having a homology of 90% or more with the amino acid sequence represented by SEQ ID NO:2 or SEQ ID NO:4 and which binds to Akt2 (to be referred to as homologous polypeptide hereinafter), or (3) a polypeptide as a protein encoded by a polynucleotide which hybridizes with the polynucleotide having the nucleotide sequence represented by SEQ ID NO:1 or SEQ ID NO:3 under a stringent condition and which binds to Akt2 (to be referred to as hybridize polypeptide hereinafter), a method for screening a substance having an insulin resistance improving action and/or a substance having carbohydrate metabolism improving action (namely diabetes mellitus improving agents) may be constructed making use of the interaction of the aforementioned polypeptides (namely the polypeptide of the present invention, the homologous polypeptide and the hybridize polypeptide) with Akt2 kinase. The polypeptide of the present invention, the aforementioned homologous polypeptide and the aforementioned hybridize polypeptide are generally referred to as a polypeptide for the screening of the present invention.

The homologous polypeptide according to this description is not particularly limited, as long as it is a polypeptide consisting of an amino acid sequence having a homology of 90% or more with the amino acid sequence represented by SEQ ID NO:2 or SEQ ID NO:4 and which binds to Akt2, but regarding the amino acid sequence represented by SEQ ID NO:2 or SEQ ID NO:4, a polypeptide consisting of an amino acid sequence having a homology of preferably 95% or more, more preferably 98% or more, is desirable.

In this connection, the aforementioned term "homology" as used in this description means a value (Identities) obtained using parameters prepared as default by Clustal program (Higgins and Sharp, *Gene,* 73, 237-244, 1998; Thompson et al., *Nucl. Acids Res.,* 22, 4673-4680, 1994) retrieval. The aforementioned parameters are as follows. As Multiple Alignment Parameters, Gap Penalty 15.00, Gap Length Penalty 6.66, Delay Divergent Seqs (%) 30 and DNA Transition Weight 0.50, and as Pairwise Alignment Parameters, Gap Penalty 15.00 and Gap Length Penalty 6.66, by Slow-Accurate.

Regarding the "stringent condition" for the hybridize polypeptide of this description under which a polynucleotide coding for the hybridize polypeptide of this description hybridizes with the polynucleotide having the nucleotide sequence represented by SEQ ID NO:1 or SEQ ID NO:3, it is a condition of "5× SSPE, 5× Denhard's solution, 0.5% SDS, 40% formamide, 200 µg/ml salmon sperm DNA, and 37° C. overnight" as the condition for hybridization, and a condition of "5× SSPE, 5× Denhard's solution, 0.5% SDS, 50% formamide, 200 µg/ml salmon sperm DNA, and 42° C. overnight" as more strict condition. Also, the condition for washing is "5× SSC, 1% SDS and 42° C." as a mild condition, "0.5× SSC, 0.1% SDS and 42° C." as a normal condition, and "0.2× SSC, 0.1% SDS and 65° C." as a more strict condition.

Also included in the screening method of the present invention is a method for screening a substance which inhibits binding of the aforementioned polypeptide with Akt2, characterized in that it comprises a step of allowing the polypeptide for screening of the present invention or a cell expressing the polypeptide for screening of the present invention or to contact a substance to be tested, a step of measuring binding of said polypeptide with Akt2, and a step of selecting a substance which inhibits the aforementioned binding. The cells expressing the polypeptide for screening of the present invention may be either cells transformed with an expression vector containing a polynucleotide coding for the polypeptide for screening of the present invention or a naturally existing cells expressing the polypeptide of the present invention, but a transformed cells are desirable.

Since the AKBP2 as one of the polypeptides for screening of the present invention binds to Akt2, its expression is reduced in diabetes mellitus model mice, and the Akt2 activity is reduced in fat cells in which mouse AKBP2 was overexpressed, it was found that the polypeptide of the present invention negatively controls the insulin signal via its binding to Akt2. Thus, an insulin resistance improving agent and/or a carbohydrate metabolism improving agent may be screened by the aforementioned screening method.

In the aforementioned screening methods, the step of measuring binding of the polypeptide for screening of the present invention or cells expressing the polypeptide for screening of the present invention with Akt2 may be carried out by directly detecting binding of the polypeptide for screening of the present invention with Akt2, or can also be carried out by measuring a change of Akt2 caused by a change of the aforementioned binding.

Though not particularly limited, examples of the substance to be tested which may be used in the screening methods of the present invention include commercially available compounds (including peptides), various conventionally known compounds registered in chemical files (including peptides), a group of compounds obtained by the combinatorial chemistry techniques (N. K. Terrett, M. Gardner, D. W. Gordon, R. J. Kobylecki and J. Steele, *Tetrahedron,* 51, 8135-73, (1995)), culture supernatants of microorganisms, natural components derived from plants and marine organisms, animal tissue extracts, or compounds (including peptides) obtained by chemically or biologically modifying a compound selected by the screening methods of the present invention.

The aforementioned screening methods are not limited, the following screening methods may be exemplified.

1) Screening Method Which Uses Phosphorylation of Akt2

It is known that the kinase activity of Akt2 is accelerated when the 473rd serine (Ser 473) or the 308th threonine (Thr 308) in the molecule is phosphorylated (*Biochem. J.*, 1998, 335 (1-13)). Making use of this, the presence or absence of Akt2 activity may be detected by detecting phosphorylated condition of the Ser 473 or Thr 308 of Akt2 by a western blotting which uses an antibody capable of specifically reacting with these phosphorylated residues (e.g., anti-phospho-Ser antibody or the like).

A testing cell expressing a part or entire portion of the polypeptide for screening of the present invention is untreated or treated with a substance to be tested. As the testing cells, cells which respond to insulin are desirable, and more illustratively, fat cells, hepatocyte or skeletal muscle-derived cells are desirable. The cell untreated or treated with a substance to be tested is lysed, and using this as a sample, phosphorylation of Akt2, namely the presence or absence the Akt2 activity, may be detected making use of western blotting, spot western blotting or the like method which uses the anti-phosphoSer antibody. Preferably, this may be detected by the method of Example 7. In this detection system, a substance used for treating a sample in which acceleration of the phosphorylation of Akt2 (namely activation of Akt2) was observed in comparison with a sample untreated with the substance to be tested may be selected as a substance which inhibits binding of the polypeptide for screening of the present invention with Akt2, and based on this, an insulin resistance improving agent and/or carbohydrate metabolism improving agent, namely a substance having diabetes mellitus-treating effect, may be screened. As such a substance, it is desirable to select a substance which shows an ED50 value of the Akt2 phosphorylation acceleration action of 10 µM or less, preferably 1 µM or less, more preferably 0.1 µM or less, in said screening method.

2) Screening Method Which Uses In Vitro Kinase Method

The Akt2 activity can also be detected by an in vitro kinase assay method in which uptake of radioactive phosphoric acid based on a substrate is measured when a histone H2B, a GSK-3 fusion protein or the like is used as the substrate of Akt2 and allowed to react with an immune precipitate of Akt2. Illustratively, a testing cells expressing a part or entire portion of the polypeptide for screenings of the present invention are untreated or treated with a substance to be tested. As the testing cells, cells which responds to insulin are desirable, and more illustratively, fat cells, hepatocyte or a skeletal muscle-derived cells are desirable. Activated Akt2 protein may be concentrated from the aforementioned cells by immunoprecipitation using an anti-Akt2 antibody. By mixing a substrate of Akt2, such as GST-crosstide (GST fusion protein of GSK3-beta sequence as a physiological substrate of Akt), with concentrated Akt2 protein, kinase activity of Akt2 may be measured and determined using phosphorylation of the substrate as the index. Preferably, this may be measured by the method described in Example 7. It is possible to use the kinase measurements as screening methods of a large number of compound, by making use of the total kinase assay methods (Waga et al., *J. immnunol. Methods*, 190, pp. 71-77, 1996). In these measuring systems, substances used for treating samples in which acceleration of the kinase activity of Akt were observed in comparison with samples untreated with the substances to be tested may be selected as substances which inhibits binding of the polypeptide for screening of the present invention with Akt2, and based on this, insulin resistance improving agents and/or carbohydrate metabolism improving agents, namely substances having diabetes mellitus-treating effects, may be screened. As such substances, it is desirable to select a substance which shows an ED50 value of the Akt2 kinase acceleration action of 10 µM or less, preferably 1 µM or less, more preferably 0.1 µM or less, in said screening methods.

3) Screening Method Which Uses Binding of the Polypeptide for Screening of the Present Invention with Akt2

Since the polypeptide for screening of the present invention negatively controls the insulin signal via its binding to Akt2, the following screening method which uses binding of the polypeptide for screening of the present invention with Akt2 as the index may be exemplified. Illustratively, testing cells expressing a part or entire portion of the polypeptide for screenings of the present invention, or a part or entire portion of the polypeptide for screening of the present invention which is fused with a tag (e.g., GST, Flag, His or the like), is untreated or treated with a substance to be tested. As the testing cells, cells which respond to insulin is desirable, and more illustratively, fat cells, hepatocyte or skeletal muscle-derived cells are desirable. The Akt2 protein and a protein binding thereto may be concentrated from the aforementioned cells by immunoprecipitation using an anti-Akt2 antibody. In this concentration step, it is desirable that the same substance to be tested used in the aforementioned treatment of cells are contained in the reaction solution. A substance to be tested which inhibits binding of the polypeptide for screening of the present invention with Akt2 may be selected by separating the thus obtained concentrated solution of Akt2 and its binding protein by polyacrylamide gel electrophoresis using a conventionally known method and measuring the amount of the polypeptide for screening of the present invention by western blotting using an antibody. As such a substance, it is desirable to select a substance which shows an IC50 value, of the action to inhibit binding of the polypeptide of the present invention with Akt2, of 10 µM or less, preferably 1 µM or less, more preferably 0.1 µM or less, in the aforementioned screening method. Regarding the antibody to be used in this case, an antibody specific for the polypeptide for screening of the present invention or for the polypeptide for screening of the present invention prepared based on its partial sequence (e.g., anti-AKBP2 antibody), or an antibody which recognizes the aforementioned tag, may be used.

In the above screening methods of 1) to 3), the testing cells may be used by un-stimulating or stimulating with insulin, but preferably, the testing cells may be used by carrying out insulin stimulation.

In addition, substances to be tested which inhibits binding of the polypeptide for screening of the present invention with Akt2 can also be selected by combining a western blotting similar to the aforementioned one with an in vitro pull down method (H. Matsushime et al., Jikken Kogaku (Experimental Engineering), Vol. 13, No. 6, p. 528, 1994, ), using Akt2 protein purified by attaching a tag (e.g., GST or the like) from an extract of cells in which the polypeptide for screening of the present invention is expressed, or a mixed solution of proteins prepared by carrying out in vitro transcription and translation, to which a substance to be tested is added or not added. Preferably, substances to be tested which inhibits binding of Akt2 with the polypeptide for screening of the present invention can also be selected using a mixed solution of proteins prepared by directly carrying out in vitro transcription and translation of a protein consisting of the polypeptide of the present invention (e.g., AKBP2 protein) as shown in Example 6, from a plasmid which expresses the polypeptide for screening of the present invention (e.g., the AKBP2 expression plasmid prepared in Example 1(5)) using an in vitro translation kit (e.g., TNT Kit (Promega)). Each of these methods renders possible screening of a large number of substances to be tested by not carrying out polyacrylamide gel electrophoresis, but carrying out conventionally known spot western blotting. Also, it is possible to carry out a screening for selecting a substance to be tested capable of inhibiting binding of Akt2 with the polypeptide for screening of the present invention, in accordance with conventionally known ELISA methods, which comprises adding a substance to be tested to a lysate of cells in which the polypeptide for screening of the present invention expressed by fusing a tag similar to the aforementioned one and Akt2 are simultaneously expressed. In addition, it is possible to select a substance to be tested which inhibits binding of Akt2 with the polypeptide for screening of the present invention by screening it from the great majority of population through the detection of the existing CAT or luciferase activity, making use of the conventionally known two hybrid system for mammal cells (Clontech), and arranging Akt2 fused with the DNA binding region of GAL 4 as the bait, and the polypeptide for screening of the present invention fused with the transcription accelerating region of VP 16 to the pray side.

<Method for Producing a Pharmaceutical Composition for Insulin Resistance Improvement and/or Carbohydrate Metabolism Improvement>

Also included in the present invention is a method for producing a pharmaceutical composition for insulin resistance improvement, characterized in that it comprises a step of carrying out screening using the polypeptide for screening of the present invention, and a step of preparing a pharmaceutical preparation.

The pharmaceutical composition which contains a substance obtained by the screening method of the present invention as the active ingredient may be prepared using carriers, fillers and/or other additive agents generally used in making pharmaceutical preparations, in response to the type of the aforementioned active ingredient.

As its administration, oral administration by tablets, pills, capsules, granules, fine subtilaes, powders, solutions for oral use or the like, or parenteral administration by injections for intravenous injection, intramuscular injection, intraarticular injection or the like, suppositories, percutaneous administration preparations, transmucosal administration preparations or the like may be cited. Particularly, parenteral injection is desirable in the case of peptides which are digested in the stomach, intravenous injection or the like.

In the solid composition for use in the oral administration, one or more active substances may be mixed with at least one inert diluent such as lactose, mannitol, glucose, microcrystalline cellulose, hydroxypropylcellulose, starch, polyvinyl pyrrolidone, aluminum magnesium silicate or the like. In the usual way, the aforementioned composition can contain other additives than the inert diluent, such as a lubricant, a disintegrating agent, a stabilizing agent, a solubilizing or solubilization assisting agent or the like. As occasion demands, tablets or pills may be coated with a sugar coating or with a film of a gastric or enteric substance or the like.

The liquid composition for oral administration can contain, for example, emulsions, solutions, suspensions, syrups, elixirs or the like and can contain a generally used inert diluent such as purified water or ethyl alcohol. The aforementioned composition can contain additive agents other than the inert diluent, such as a moistening agent, a suspending agent, a sweetener, an aromatic, or an antiseptic.

The injections for parenteral administration can include aseptic aqueous or non-aqueous solutions, suspensions or emulsions. The aqueous solutions or suspensions can include, for example, distilled water for injection, physiological saline or the like as the diluent. As the diluent for use in the non-aqueous solutions or suspensions, propylene glycol, polyethylene glycol, plant oil (e.g., olive oil), alcohols (e.g., ethanol), polysorbate 80 or the like can for example be included. The aforementioned composition can further contain, a moistening agent, an emulsifying agent, a dispersing agent, a stabilizing agent, a solubilizing or solubilization assisting agent, an antiseptic or the like. The aforementioned composition may be sterilized, for example, by filtration through a bacteria retaining filter, blending of a germicide or irradiation. Alternatively, it may be used by producing a sterile solid composition and dissolving it in sterile water or other sterile solvent for injection prior to its use.

The dose may be optionally decided by taking into consideration strength of activity of the active ingredient, namely the substance obtained by the screening method of the present invention, symptoms, age, sex and the like of each patient to be treated.

For example, in the case of oral administration, the dose is generally approximately from 0.1 to 100 mg, preferably from 0.1 to 50 mg, per day per adult (as 60 kg body weight). In the case of parenteral administration in the form of injections, it is from 0.01 to 50 mg, preferably from 0.01 to 10 mg, per day.

EXAMPLES

The present invention is described in the following based on examples, but the invention is not restricted by said examples. In this connection, unless otherwise noted, these may be carried out in accordance with conventionally known methods ("Molecular Cloning, Sambrook et al., Cold Spring Harbor Laboratory Press, 1989" and the like). Also, when commercially available reagents and kits are used, these may be carried out in accordance with the instructions attached thereto.

Example 1

Cloning of Mouse AKBP2 Gene and Construction of Expression Vector (1) Cloning of Akt2 Gene Using the oligonucleotides represented by SEQ ID NO:5 and SEQ ID NO:6, designed with reference to the cDNA sequence described in the accession number M95936 of a gene data base GenBank, as primers, and a human skeletal muscle cDNA (Marathon-Ready™ cDNA; Clontech) as the template, PCR was carried out using a DNA polymerase (Pyrobest DNA Polymerase (Takara Shuzo)) under a condition of thermal denaturation at 95° C. for 3 minutes, 40 repetition of a cycle consisting of 98° C. for 10 seconds, 60° C. for 30 seconds and 74° C. for 1 minute and 30 seconds, and further heating at 74° C. for 7 minutes. Human Akt2 cDNA was cloned by inserting the resulting DNA fragment of about 1.5 kbp into the EcoRV recognition site of a plasmid pZErO™-2.1 (Invitrogen). Nucleotide sequence of the Akt2 cDNA cloned on the vector was determined by a sequencing kit (Applied Biosystems) and a sequencer (ABI 3700 DNA sequencer, Applied Biosystems), using the aforementioned oligonucleotides represented by SEQ ID NO:5 and SEQ ID NO:6, thereby confirming that its sequence coincided with the reported sequence.

(2) Preparation of Expression Plasmid for Yeast Two Hybrid

In order to insert the human Akt2 cDNA into an expression vector for yeast two hybrid, pDBtrp (Invitrogen), primers represented by SEQ ID NO:7 and SEQ ID NO:8 were designed by adding a region homologous with 40 nucleotides in front and in the rear of the pDBtrp vector multi-cloning site to the 5'-side and 3'-side of the human Akt2 gene sequence. PCR was carried out using the Akt2 plasmid cloned in the above as the template and using a DNA polymerase (Pyrobest DNA polymerase; Takara Shuzo), by heating at 98° C. (1 minute) and then repeating 35 times of a cycle consisting of 98° C. (5 seconds), 55° C. (30 seconds) and 72° C. (5 minutes) The DNA fragment obtained as the result has the complete code region of the human Akt2 gene.

The vector pDBtrp made into a linear chain by digesting with restriction enzymes SalI and NcoI and the PCR fragment containing Akt2 cDNA obtained in the above were simultaneously added to yeast strain MaV203 for two hybrid (Invitrogen) which was then transformed by a lithium acetate method (Guthrie C. and Fink R., Guide to Yeast Genetics and Molecular Biology, Academic, San Diego, 1991). As a result, homologous recombination occurred in the yeast cell, and a plasmid in which the Akt2 cDNA was inserted into the multicloning site of pDBtrp (to be referred to as pDB-Akt2 hereinafter) was formed. Yeast cell having the pDB-Akt2 plasmid were selected by culturing on a solid synthetic minimal medium (DISCO,20% agarose) from which tryptophan as a selection marker of the plasmid had been deleted, the yeast cells were treated with zymolyase (Seikagaku Kogyo) at 37° C. for 30 minutes, and then the plasmids were isolated and purified by the alkali method, and determination of their nucleotide sequences was carried out using a sequencing kit (Applied Biosystems) and a sequencer (ABI 3700 DNA sequencer, Applied Biosystems) to select those in which the Akt2 cDNA was inserted together with the code region and translation frame of GAL 4 DNA binding region of pDBtrp.

(3) Preparation of Mouse Fat Tissue Derived cDNA Library

By purchasing C57BL/6J male mice of 12 weeks of age and C57BL/KsJ-+m/+m male mice of 13 weeks of age from CLEA Japan, Poly(A)+ RNA was prepared from epididymis fat in accordance with the mRNA preparation method described in Experimental Medicine Supplement, Bio-manual Series 2, Gene Library Preparation Method (written in Japanese, edited by H. Nojima; published by Yohdosha on Feb. 20, 1994). Using ZAP-cDNA Synthesis Kit manufactured by Stratagene and in accordance with the protocol attached thereto, first-strand synthesis and second-strand synthesis were carried out using 5 µg of RNA, and the double-stranded cDNA was smooth-ended, ligated with the EcoRI adapter attached to the kit and then digested with restriction enzymes EcoRI and XhoI. Size fractionation was carried out using a spin column (CHROMA SPIN-400; Clontech), and shorter fragments were removed. A 100 µg portion of a vector pACT2 (Clontech) was digested with the restriction enzyme XhoI, treated with an alkaline phosphatase (Bacterial Alkaline Phosphatase; Takara Shuzo), and then digested with the restriction enzyme EcoRI and applied to a spin column (CHROMA SPIN-1000; Clontech). In accordance with the cDNA library preparation method described in Experimental Medicine Supplement, Bio-manual Series 2, Gene Library Preparation Method (edited by H. Nojima; published by Yohdosha on Feb. 20, 1994), the vector and cDNA were ligated, and the sample after ligation was treated with a filter cup (UFCP3TK50) manufactured by Millipore. Using the Escherichia coli for electroporation manufactured by GIBCO BRL (ElectroMAXX DH10B™ Cells), transformation was carried out by the electroporation method, and cultured overnight on a shaker using 1,000 ml of a culture medium. After confirming that $10^6$ or more of independent colonies are present in the culture medium, plasmids were purified using a plasmid purification kit (Qiagen Plasmid Kit; Qiagen) and in accordance with the protocol attached to the kit.

(4) Yeast Two Hybrid Screening

The aforementioned yeast strain MaV203 for two hybrid transformed by pDB-Akt2 was suspended in 400 ml of YPD liquid medium (DIFCO), cultured at 30° C. for about 6 hours until absorbance at a wave length of 590 nanometer became from 0.1 to 0.4, and then made into competent cells by the lithium acetate method, and the final amount was suspended in 1.0 ml of 0.1 M lithium-tris buffer. The cells were transformed with 20 µg of the mouse fat tissue derived cDNA library prepared in the aforementioned (3), and the cells were selected by culturing on a solid synthetic minimal medium (DISCO, 20% agarose) from which tryptophan and leucine as respective selection markers of pDB-Akt2 and the library had been deleted, thereby obtaining a transformant into which both plasmids were introduced. At the same time, in order to select a cell having an activated reporter gene HIS3 which is expressed when a fusion protein of the GAL4 DNA binding domain artificially expressed in the two hybrid system is linked to a fusion protein of the GAL4 transcriptional activation domain, the transformed cells were cultured at 30° C. for 5 days on the solid minimal medium (20% agarose) from which histidine was removed together with tryptophan and leucine and to which 20 mM of 3AT (3-amino-1,2,4-triazole; Sigma) as an inhibitor of the enzyme encoded by HIS3 was added. The 3AT-resistant yeast colonies showing that a protein which binds to Akt2 is expressed under the same condition were obtained. These yeast cells were grown on the YPD solid medium for 24 hours, and then expression of the lacZ gene which is different from HIS3 but is a binding indicator reporter of the two hybrid system was examined using β-galactosidase activity as the index. Regarding the β-galactosidase activity, yeast cells on the medium were transferred on a nitrocellulose film, frozen in liquid nitrogen and then thawed at room temperature, and the filter was put on a filter paper soaked with 0.4% X-GAL (Sigma) solution and allowed to stand at 37° C. for 24 hours to measure change of color to blue caused by β-galactosidase. By selecting colonies in which contents of cells transferred on the filter changed from white to blue, yeast cells expressing a protein which binds to Akt2 were specified, and library derived plasmids were extracted from the cells in accordance with the method of Yeast Protocols Handbook of Clontech. Nucleotide sequences of the gene fragments contained therein were determined by a sequencing kit (Applied Biosystems) and a sequencer (ABI 3700 DNA sequencer, Applied Biosystems) using the nucleotide sequence represented by SEQ ID NO:9 (a sequence which binds to the GAL4 AD region; derived from GenBank accession number U29899 Cloning vector pACT2) as the primer, and it was confirmed as a result that the nucleotide sequence represented by SEQ ID NO:1 was contained therein.

(5) Determination of Initiation Codon of Mouse AKBP2 Gene

As a result of the aforementioned (4), a library derived plasmid having a gene fragment containing the nucleotide sequence represented by SEQ ID NO:1 was obtained. Accordingly, in order to determine initiation codon of the gene contained in said fragment, a primer of the nucleotide sequence represented by SEQ ID NO:10 which corresponds to a complementary chain of a nucleotide sequence of from the 1034th position to the 1011th position of the nucleotide sequence represented by SEQ ID NO:1 was synthesized (Proligo), and an attempt was made to amplify complete length cDNA derived from an expression product of said gene from the aforementioned fat tissue-derived cDNA library by PCR using said primer and the aforementioned primer of the nucleotide sequence represented by SEQ ID NO:9. The PCR was carried out using a DNA polymerase (TAKARA LA Taq; Takara Shuzo) and by heating at 94° C. (3 minutes) and then repeating 35 times of a cycle consisting of 94° C. (30 seconds), 58° C. (1.5 minutes) and 72° C. (4 minutes). The DNA fragments in the reaction solution were cloned into an expression vector (pcDNA3.1/V5-His-TOPO; Invitrogen) using TOPO TA Cloning System (Invitrogen). Nucleotide sequences of the inserted DNA fragments in the thus obtained plasmids were determined using a primer (TOPO TA Cloning Kit; Invitrogen; SEQ ID NO:11) which binds to the T7 promoter region on the vector, a sequencing kit (Applied Biosystems) and a sequencer (ABI 3700 DNA sequencer, Applied Biosystems). As a result, plasmids containing cDNA molecules of various lengths having the sequence of said gene were obtained, but chain lengths of the longest cDNA molecules were almost the same as that of the transcription product derived cDNA obtained in the aforementioned (4). Since several trials showed the same result, it was found that the chain length of sequence of the transcription product of said gene almost coincide with those of the cDNA obtained in (4). Based on this, it was found that the first ATG of the nucleotide sequence represented by SEQ ID NO:1 is the initiation codon of said gene, so that the open reading frame of said gene represented by SEQ ID NO:1 was confirmed. This gene was named mouse AKBP2 gene.

(6) Preparation of Mouse AKBP2 Expression Vector

As a result of the aforementioned (4), a library-derived plasmid having a gene fragment containing complete length of the nucleotide sequence represented by SEQ ID NO:1 was obtained, and the presence of a factor which binds to Akt2 was indicated. Also, its open reading frame was confirmed in the aforementioned (5). Accordingly, the primers represented by SEQ ID NO:12 and SEQ ID NO:13 were synthesized (Proligo) in accordance with the nucleotide sequence information shown in SEQ ID NO:1, and an AKBP2 cDNA coding for the net AKBP2 protein was amplified by PCR using said primers and the plasmid obtained in the aforementioned (4) as the template. These two kinds of DNA primers respectively have nucleotide sequences homologous with partial sequences of the 5'-side and 3'-side of the mouse AKBP2 gene represented by SEQ ID NO:1. PCR was carried out using a DNA polymerase (Pyrobest DNA Polymerase; Takara Shuzo), by heating at 98° C. (1 minute) and then repeating 35 times of a cycle consisting of 98° C. (5 seconds), 55° C. (30 seconds) and 72° C. (5 minutes) As a result of separating the PCR product by an agarose gel electrophoresis, it was confirmed that a DNA fragment of about 1.7 kbp was amplified. Accordingly, this DNA fragment in the reaction solution was subcloned into an expression vector (pcDNA3.1/V5-His-TOPO; Invitrogen) using TOPO TA Cloning System (Invitrogen). The primer represented by SEQ ID NO:13 used in this case was designed in such a manner that the stop codon sequence of AKBP2 was removed so that a vector-derived V5 epitope (derived from V protein of paramyxovirus SV 5, Southern J. A., *J. Gen. Virol.*, 72, 1551-1557, 1991) and His 6 tag (Lindner P., *BioTechniques*, 22, 140-149, 1997) were continued with the same frame of the triplet of mouse AKBP2 gene at the 3'-side after cloning. Nucleotide sequence of the inserted DNA fragment in the thus obtained plasmid was determined using a primer (TOPO TA Cloning kit; Invitrogen; SEQ ID NO:11) which binds to the T7 promoter region on the vector, a sequencing kit (Applied Biosystems) and a sequencer (ABI 3700 DNA sequencer, Applied Biosystems). As a result, it was confirmed that the 1719 base pair AKBP2 cDNA represented by SEQ ID NO:1 coding for the net AKBP2 protein was inserted into the aforementioned expression vector pcDNA3.1/V5-His-TOPO, as a DNA from which the 3'-side stop codon of the DNA sequence was removed. This expression plasmid is referred to as pcDNA-AKBP2 hereinafter.

Example 2

Preparation of Cultured Cell Which Expresses AKBP2 Protein (1) Preparation of AKBP2 Expression Cell The aforementioned expression plasmid pcDNA-AKBP2 prepared in Example 1(5) or an empty vector (pcDNA3.1/V5-His-TOPO) was introduced into the 293 cell (Cell Bank). The 293 cell was cultured in a culture dish of 6 well culture plate (well diameter 35 mm) until it became a state of 70% confluent, by adding 2 ml of a minimal essential medium DMEM (Gibco) containing 10% fetal bovine serum (Sigma) to each well. The pcDNA-AKBP2 (3.0 μg/well) was transiently introduced into this cell by the calcium phosphate-method (Graham et al., Virology, 52, 456, 1973; N. Arai, Gene Transfer and Expression/Analytical Method (written in Japanese), pp. 13-15, 1994). After 30 hours of culturing, the medium was removed and the cells were washed with phosphate buffered saline (to be referred to as PBS hereinafter), and then the cells were lysed by adding 0.1 ml per well of a cell lysis solution (100 mM potassium phosphate (pH 7.8), 0.2% Triton X-100).

(2) Detection of AKBP2 Protein

A 10 μl portion of 2× SDS sample buffer (125 mM Tris-HCl (pH 6.8), 3% sodium lauryl sulfate, 20% glycerol, 0.14 M β-mercaptoethanol, 0.02% Bromophenol Blue) was added to 10 μl of the aforementioned lysate of AKBP2 expression cell of Example 2(1), and this was treated at 100° C. for 2 minutes and then subjected to 10% SDS polyacrylamide gel electrophoresis to separate proteins contained in the sample. Proteins in the polyacrylamide gel were transferred on a nitrocellulose membrane using a semi-dry type blotting device (Bio-Rad), and then detection of the AKBP2 protein on said nitrocellulose membrane was carried out by western blotting in accordance with the usual way. A monoclonal antibody (Invitrogen) which recognizes V5 epitope fused to the C-terminus of AKBP2 was used as the primary antibody, and mouse IgG-HRP fusion antibody (Bio-Rad) was used as the secondary antibody. As a result, as shown in FIG. 1, it was confirmed that a protein of about 70 kDa which corresponds to an AKBP2-V5-His 6 fusion protein consisting of 618 amino acids containing the C-terminal side tag consisting of 45 amino acid is detected dependently on the gene transfer of the expression vector pcDNA-AKBP2. Based on this, it was revealed that complete length region of the aforementioned mouse AKBP2 gene cloned is certainly expressed and can form stable structure as the protein in the cultured cell.

Example 3

Measurement of AKBP2 Expression Level in Normal Mice, High Fat Diet-loaded Normal Mice and Diabetes Mellitus Model Mice Based on the aforementioned information, it was found that the mouse AKBP2 protein of the present invention binds to Akt2, and is expressed in the insulin-responding tissues including both adipose and muscle. Since Akt2 protein is a factor which acts upon the insulin signal first pathway, it was considered that action of the AKBP2 of the present invention is related to the insulin resistance. Accordingly, measurement of messenger RNA (mRNA) expression level of the AKBP2 gene in muscle and fat was carried out using a type 2 diabetes mellitus model mice KKA$^y$/Ta (Iwatsuka et al., Endocrinol. Japon.: 17, 23-35, 1970, Taketomi et al., Horm. Metab. Res., 7, 242-246, 1975) and a healthy mice C57BL/6J fed with a normal feed or a high fat diet.

Regarding the gene expression level, expression level of the mouse AKBP2 gene of the present invention was measured and corrected by the simultaneously measured expression level of glyceraldehyde 3-phosphate dehydrogenase (G3PDH) gene. As the measuring system, PRISM™ 7700 Sequence Detection System and SYBR Green PCR Master Mix (Applied Biosystems) were used. In this measuring system, expressed amount of the gene of interest is determined by detecting and monitoring fluorescence level of the SYBR Green I pigment incorporated by double-stranded DNA amplified by PCR in a real time manner.

Illustratively, the measurement was carried out by the following procedures.

(1) Preparation of Total RNA

C57BL/6J male mice of 14 weeks of age loaded with a usual feed or a high fat diet, and C57BL/6J male mice and KKA$^y$/Ta mice of 15 weeks of age (all from CLEA Japan) were used. The high fat diet loading was carried out for 9 weeks from 5 weeks of age to 14 weeks of age. Composition of the high fat diet is as follows: casein 29.8%, sucrose 15.8%, vitamin mix 1.3%, mineral mix 8.8%, cellulose powder 5.0%, methionine 0.5%, safflower oil 28.9%, water 10%. On the other hand, CE-2 (CLEA Japan) was used as the normal feed. Muscle and fat of each of the aforementioned mice were extracted, and total RNA was prepared using a reagent for RNA extraction (Isogen; Nippon Gene) and in accordance with its instructions. Each total RNA thus prepared was then treated using deoxyribonuclease (Nippon Gene), subjected to phenol/chloroform treatment and ethanol precipitation, dissolved in sterile water and stored at −20° C.

(2) Synthesis of Single-stranded cDNA

Reverse transcription of total RNA into single-stranded cDNA was carried out in a system of 20 μl using 1 μg of RNA (fat), 1 μg of RNA (muscle of a mouse of 14 weeks of age) or 0.25 μg of RNA (muscle of a mouse of 15 weeks of age) prepared in (1), and using a kit for reverse transcription reaction (Advantage™ RT-for-PCR Kit; Clontech). After the reverse transcription, this was mixed with 180 μl of sterile water and stored at −20° C.

(3) Preparation of PCR Primers

Four oligonucleotides (SEQ ID NO:14 to SEQ ID NO:17) were designed as the PCR primers described in the following item (4). They were used as a combination of SEQ ID NO:14 with SEQ ID NO:15 for the mouse AKBP2 gene, and a combination of SEQ ID NO:16 with SEQ ID NO:17 for the G3PDH gene.

(4) Measurement of Gene Expression Quantity

Real time measurement of PCR amplification by PRISM™ 7700 Sequence Detection System was carried out in a system of 25 μl in accordance with the instructions. In each system, 5 μl of single-stranded cDNA, 12.5 μl of 2× SYBR Green reagent and 7.5 pmol of each primer were used. In this case, the single-stranded cDNA preserved in (2) was used by diluting 30 times regarding the G3PDH, or by diluting 10 times regarding the mouse AKBP2. Instead of the single-stranded cDNA, 0.1 μg/μl of a mouse genomic DNA (Clontech) was appropriately diluted and a 5 μl portion thereof was used for the preparation of calibration curve. PCR was carried out by heating at 50° C. for 10 minutes, subsequently heating at 95° C. for 10 minutes, and then repeating 45 cycles of a process consisting of 2 steps of 95° C. for 15 seconds and 60° C. for 60 seconds.

Expressed amount of the mouse AKBP2 gene in each sample was corrected by the expressed amount of G3PDH gene based on the following formula.

[Corrected amount of *AKBP2* expression]=[expressed amount of *AKBP2* (raw data)]/[expressed amount of *G3PDH* (raw data)]

FIG. 2 shows relative amounts in which the expressed amount in C57BL/6J mouse of usual feed was defined as 1 in comparing expressed amounts in fat, and the expressed amount in C57BL/6J also as 1 in comparing expressed amounts in muscle tissue.

As shown in FIG. 2, it was confirmed that expression of the mouse AKBP2 gene of the present invention is markedly increased in the fat and muscle at the time of high fat diet loading, or in the fat and muscle of the diabetes mellitus model mouse. Accordingly, it is considered that the mouse AKBP2 of the present invention induces insulin resistance by the acceleration of expression quantity in fat and muscle. Based on the above, it may be concluded that concern of the mouse AKBP2 of the present invention in the insulin resistance is large.

In addition, it was revealed from the results of this Example that diagnosis of diabetes mellitus morbid state may be made by measuring expression quantity of mouse AKBP2.

Example 4

Cloning of Human AKBP2 Gene, and Its Expression Distribution Analysis in Various Tissues An attempt was made on the amplification of AKBP2 human orthologue gene complete length cDNA by the same PCR method shown in the aforementioned Example 1(5), using a human fat-derived cDNA library (Clontech) as the template and a pair of primers represented by SEQ ID NO:18 and SEQ ID NO:19. When nucleotide sequence of a DNA fragment of about 1.8 kbp obtained as a result thereof was determined in accordance with the same method shown in Example 1, it was confirmed that it contains complete length cDNA of the gene represented by SEQ ID NO:3. Said gene cDNA is a novel gene which encodes the polypeptide represented by SEQ ID NO:4. Said gene is a human orthologue gene of AKBP2 in which it has a homology of 76.8% with the mouse AKBP2 gene represented by SEQ ID NO:1, and the encoded polypeptide has a homology of 71.3% with the mouse AKBP2 protein represented by SEQ ID NO:2, respectively.

Accordingly, an attempt was subsequently made to amplify a cDNA fragment of about 800 bases of the 3'-side of the human AKBP2 gene from cDNA samples derived from various human tissues, by PCR using the primer represented by SEQ ID NO:20 newly designed based on the sequence of said human AKBP2 gene and the aforementioned primer represented by SEQ ID NO:19, and the presence or absence of the expression of AKBP2 in respective tissues was examined. The PCR was carried out by DNA polymerase (Pyrobest DNA polymerase; Takara shuzo) using 2 μg of each of the various human tissue cDNA libraries (Clontech) as the template and, after heating at 98° C. (1 minute), repeating 35 cycles each cycle consisting of 98° C. (5 seconds), 55° C. (30 seconds) and 72° C. (5 minutes). When the thus obtained PCR products were separated by an agarose gel electrophoresis, a desired DNA fragment of about 800 base pair considered to be containing a 3'-terminal side partial sequence of the human AKBP2 gene was amplified from each of the skeletal muscle-, liver- and fat-derived cDNA libraries. When these DNA fragments were separated from respective agarose gels, and nucleotide sequences of said DNA fragments were respectively determined in accordance with the method described in the aforementioned Example 1(4) using the primer represented by SEQ ID NO:20, it was confirmed that they are the 3'-terminal side partial sequence of human AKBP2 gene represented by SEQ ID NO:3. Based on this, it was revealed that expression of the human AKBP2 gene is specifically controlled in fat, muscle, liver and the like limited organs which respond to the insulin signal.

As a result of this Example, since the human AKBP2 showed high homology with mouse AKBP2 and its expression was observed in insulin responding tissues, it was confirmed that it has the same functions of those of the mouse counterpart and therefore is useful for the diagnosis of diabetes mellitus and screening of a diabetes mellitus improving agent.

Example 5

Preparation of Cultured Cells Which Express Human AKBP2 Protein

The aforementioned AKBP2 gene complete length cDNA obtained in Example 4 was subcloned by the same method shown in the aforementioned Example 1(6). Thereafter, it was confirmed that the 1782 base pair human AKBP2 cDNA represented by SEQ ID NO:3 coding for the net human AKBP2 protein was inserted into the aforementioned expression vector pcDNA3.1/V5-His-TOPO, as a DNA from which the 3'-side stop codon of the DNA sequence was removed. This expression plasmid is referred to as pcDNA-human AKBP2 hereinafter. By introducing 5.1 µg per well of this expression plasmid pcDNA-human AKBP2 by the same method of Example 2(1), expression of human AKBP2 protein was detected in accordance with the method of Example 2(2). As a result, it was confirmed that a protein of about 70 kDa which corresponds to a human AKBP2-V5-His 6 fusion protein consisting of 638 amino acids containing the C-terminal side tag consisting of 45 amino acid is detected dependently on the gene transfer of the expression vector pcDNA-human AKBP2, so that it was revealed that the complete length region of the aforementioned cloned human AKBP2 gene is certainly expressed in the cultured cells and can form stable structure as the protein.

Example 6

Inspection of Interaction Between Human AKBP2 and Akt2

(1) Preparation of GST Fusion Akt2 Expression Plasmid

In order to insert human Akt2 cDNA into a GST fusion expression vector pGEX-3X (Amersham Bioscience), the human Akt2 cDNA obtained in Example 1(1) was digested with restriction enzymes HindIII and EcoRI, and the vector PGEX-3X with restriction enzymes BamHI and EcoRI, respectively, thereby making them into linear chains. In addition, in order to use the fragments represented by SEQ ID NO:21 and SEQ ID NO:22 as fragments for their ligation, they were separately treated at 60° C. for 30 minutes as a pretreatment and then mixed and allowed to stand at room temperature for 2 hours. A mixture of these treated human Akt2 cDNA fragment, vector pGEX-3X and fragment for ligation was mixed with a DNA ligase solution (DNA ligation kit II; Takara Shuzo) and treated at 16° C. for 3 hours, thereby preparing a plasmid in which Akt2 cDNA was inserted into the multi-cloning site of pGEX-3X (to be referred to as pGEX-Akt2 hereinafter). By carrying out determination of the nucleotide sequence using the oligonucleotide represented by SEQ ID NO:23 as a primer and using a sequencing kit (Applied Biosystems) and a sequencer (ABI 3700 DNA sequencer, Applied Biosystems), those in which the code region of Akt2 cDNA and the GST tag translation frame of pGEX vector were inserted in union were selected.

(2) Purification of GST Fusion Akt2 Protein

Using the plasmid pGEX-Akt2 obtained in the aforementioned (1), *Escherichia coli* BL21 was transformed by the heat shock method and cultured overnight on a shaker using 2.4 ml of a culture medium, total volume thereof was inoculated into 400 ml of a culture medium and cultured at 37° C. for 3 hours on a shaker, and then IPTG (SIGMA) was added thereto to a final concentration of 2.5 mM and the shaking culturing was further continued for 3 hours to induce expression of the GST fusion Akt2 protein (to be referred to as GST-Akt2 hereinafter). By recovering the cells, GST-Akt2 was purified on glutathione Sepharose beads (Glutathione Sepharose 4B; Amersham Pharmacia) in accordance with a conventionally known method (H. Matsushime et al., Jikken Kogaku (Experimental Engineering), Vol. 113, No. 6, p. 528, 1994). As a control, a protein of GST moiety alone (to be referred to as GST protein hereinafter) was expression-induced and purified from the *Escherichia coli* BL21 transformed with pGEX-3X, in the same manner as in the above. By carrying out separation by SDS polyacrylamide gel electrophoresis and Coomassie Brilliant Blue staining in accordance with conventionally known methods, it was confirmed that the proteins having expected molecular weights (GST-Akt2; 79 kDa, GST protein; 26 kDa) were purified.

(3) Verification of Biochemical Binding of Akt2 Protein with Human AKBP2 Protein Using the GST fusion Akt2 protein (to be referred to as GST-Akt2 hereinafter) prepared in the aforementioned (2), the presence or absence of direct interaction between human AKBP2 protein and Akt2 protein was verified by the GST-pull down method (H. Matsushime et al., Jikken Kogaku, Vol. 113, No. 6, p. 528, 1994). Firstly, using 0.5 µg of the pcDNA-human AKBP2 prepared in the aforementioned Example 5 as the template, and using 40 µl of a TNT kit (TNTR Quick Coupled Transcription/Translation System; Promega) and 1.3 MBq of a radioisotope (redivue Pro-mix L-[$^{35}$S]; Amersham), radioisotope-labeled human AKBP2 protein was prepared by in vitro transcription and translation in accordance with the attached protocols. A 15 µl portion of this human AKBP2 protein preparation solution was mixed with 1 µg of the GST protein or GST-Akt2 purified on glutathione beads in the aforementioned (2) and shaken at 4° C. for 1 hour after adding 0.3 ml of Buffer A (50 mM Tris-HCl (pH 7.5), 10% glycerol, 120 mM NaCl, 1 mM EDTA, 0.1 mM EGTA, 0.5 mM PMSF, 0.5% NP-40). Thereafter, the protein which binds to GST protein or GST-Akt2 on beads was co-precipitated by centrifugation. This was suspended in 0.5 ml of a buffer solution in which the NaCl concentration of the aforementioned Buffer A was changed to 100 mM, and again co-precipitated by centrifugation. After repeating this operation 4 times, proteins in the precipitate were separated by SDS polyacrylamide gel electrophoresis in accordance with a conventionally known method, and the human AKBP2 protein was detected by autoradiography. As a result, a band which is not detected when the GST protein is mixed was detected when GST-Akt2 was mixed. Based on this, it was revealed that the human AKBP2 as one of the polypeptides of the present invention interacts with Akt2 protein similar to the case of the mouse AKBP2 of the present invention, thus proving that these human and mouse AKBP2 molecules are counterparts which carry out the same function in both animal species. Accordingly, it was found that the human AKBP2 of the present invention is concerned in the induction of insulin resistance via its interaction with Akt2 protein similar to the case of the mouse AKBP2 of the present invention.

Example 7

Influence of Mouse AKBP2 Over-expression in NIH3T3 L1 Fat Cell Upon Akt2 Kinase Activity From the results of the aforementioned yeast two hybrid and biochemical binding analyses, it was shown that Akt2 and AKBP2 interact with each other. Accordingly, influence of AKBP2 upon the enzyme (kinase) activity of Akt2 was examined by an in vitro kinase assay using a cultured cell NIH3T3 L1.

(1) Preparation of Substrate GST-crosstide for In Vitro Kinase Assay

The synthetic oligo DNA molecules represented by SEQ ID NO:24 and SEQ ID NO:25 coding for the phosphorylation region of GSK3p which is a physiological substrate of Akt2 were mixed and integrated into the EcoRI XhoI site of the pGEX-6P-1 vector. This was used as GST-crosstide. Using the plasmid GST-crosstide, *Escherichia coli* BL21 was transformed by the heat shock method and cultured overnight on a shaker using 2.4 ml of a culture medium, total volume thereof was inoculated into 400 ml of a culture medium and cultured at 37° C. for 3 hours on a shaker, and then IPTG (SIGMA) was added thereto to a final concentration of 2.5 mM and the shaking culturing was further continued for 3 hours to induce expression of a GST fusion protein (to be referred to as GST-crosstide hereinafter). By recovering the cells, GST-crosstide was purified on glutathione Sepharose beads (Glutathione Sepharose 4B; Amersham Pharmacia) in accordance with a conventionally known method (H. Matsushime et al., Jikken Kogaku (Experimental Engineering), Vol. 113, No. 6, p. 528, 1994). By carrying out separation of these proteins by SDS polyacrylamide gel electrophoresis and their Coomassie Brilliant Blue staining in accordance with conventionally known methods, it was confirmed that the GST-crosstide was purified.

(2) Preparation of AKBP2 High Expression Virus Making Use of Adenovirus Vector

A gene fragment coding for mouse AKBP2 was cut out from the pcDNA-AKBP2 vector using restriction enzymes BamHI and SacII and inserted into the multi-cloning site (for BGlII and NotI) of an adenovirus vector pAdTrack-CMV (obtained from Johns Hopkins Cancer Center) using linker oligo SEQ ID NO:26 and SEQ ID NO:27 which form SacII and NotI digestion fragments, thereby obtaining a vector AKBP2/pAdTrack-CMV.

Thereafter, preparation of a solution of high titer adenovirus capable of expressing AKBP2 was carried out in accordance with a conventionally known protocol ["A Practical Guide for using the AdEasy System" www.coloncancer.org/adeasy.htm" "www.coloncancer.org/adeasy/protocol2.htm")]. The adenovirus for control was prepared from pAdTrack-CMV.

In this connection, regarding the amount of virus, absorbance at 260 nm (A260) was measured and converted by the following formula.

$$1\ A260=1.1\times10^{12}\ \text{virus particles}=3.3\times10^{11}\ pfu/ml \quad \text{[Formula]}$$

(3) Over-expression of Mouse AKBP2 in NIH3T3 L1 Fat Cells and Immunoprecipitation of Akt2

NIH3T3 L1 cells were suspended in Dulbecco's modified Eagle's medium (DMEM) containing 10% fetal calf serum (FCS) and inoculated in $8\times10^5$ cells/well potions into a collagen-coated 6 well plate (Asahi Techno Glass). On the next day, the medium was exchanged with the DMEM (10% FCS) further supplemented with 10 µg/ml of insulin, 250 nM of dexamethasone and 0.5 mM of 3-isobutyl-1-methylxanthine (IBMX) to induce differentiation of 3T3-L1 cells. Two days thereafter, the medium was returned to 0.4 ml of DMEM (10% FCS). Four days thereafter, an adenovirus which expresses AKBP2 was added to the medium at a concentration of $8\times10^{10}$ pfu per well. As a control, an adenovirus which expresses GFP alone was used.

After 36 hours of the adenovirus infection, the cells were cultured for 16 hours using serum-free DMEM medium, stimulated with 100 nM of insulin for a predetermined period of time (0, 30 or 60 minutes) and then immediately dissolved in 500 µl of a cell lysis solution (50 mM Tris-HCl pH 7.5, 1 mM EDTA, 5 mM EGTA, 0.5 mM $Na_3VO_4$, 0.1% 2-mercaptoethanol, 50 mM NaF, 5 mM sodium pyrophosphate, 10 mM β-glycerophosphate, 1% Triton X-100, 0.1 mM PMSF). After centrifugation at 15,000 rpm for 20 minutes, the supernatant was mixed with an anti-Akt2 antibody (Upstate) and Protein G-Sepharose (Amersham) to effect immunoprecipitation. The immune precipitate was washed twice with the cell lysis solution, twice with a washing solution (50 mM Tris-HCl pH 7.5, 0.03% Brij 35, 0.1% 2-mercaptoethanol) and then twice with a reaction solution (20 mM MOPS pH 7.2, 10 mM $MgCl_2$, 25 mM β-glycerophosphate, 5 mM EDTA, 1 mM DTT) and subjected to the kinase reaction.

(4) In Vitro Kinase Assay

The aforementioned immune precipitate was suspended in 20 µl of the reaction solution. The reaction solution further supplemented with 15 µM of ATP, 10 µCi of $[\gamma^{32}P]$-ATP and 3 µg of GST-crosstide was added thereto and heated at 30° C. for 20 minutes. The reaction was stopped by adding 10 µl of 4× SDS sample buffer. After separation by SDS polyacrylamide gel electrophoresis, the radioactivity incorporated into GST-crosstide was determined by analyzing it by BAS 2000 Bioimaging Analyzer (Fuji Photo Film). As shown in FIG. 3, the kinase activity of Akt2 in the NIH3T3 L1 cell was reduced by over-expression with AKBP2 to 0.82 times as compared with the control (GFP) under insulin-un-stimulated state. In the same manner, when activity increase of Akt2 by the 100 nM insulin stimulation was observed, the GFP-infected cells showed 1.39 times (30 minutes) and 1.5 times (60 minutes) increase in the enzyme activity in comparison with the un-stimulated state, while the cells infected with the AKBP2 virus showed only 1.30 times (30 minutes) and 1.22 times (60 minutes) of the stimulation dependent increase in the activity. Also, since phosphorylation of the 473rd serine is important for the activation of Akt2, the aforementioned Akt2 immuno-precipitated after the insulin stimulation was analyzed by western blotting using an anti-phosphorylated serine473 antibody (New England Biolab) to find that the phosphorylated state at the time of no stimulation was reduced in the cells infected with the AKBP2 virus in comparison with the control virus-infected cells. In addition, a stimulation-dependent acceleration of phosphorylation was found by 30 minutes of insulin stimulation in both of the cells infected with the AKBP2 virus and the control virus-infected cells, but degree of the phosphorylation acceleration was weakened in the cells infected with the AKBP2 virus than in the control virus-infected cells, so that the results of the in vitro kinase assay was supported. Based on the above results, it is considered that the mouse AKBP2 of the present invention interacts with Akt2 and induces insulin resistance by reducing increase of the insulin-dependent enzyme activity, in addition to the insulin-independent enzyme activity.

INDUSTRIAL APPLICABILITY

The polypeptides and polynucleotides of the present invention which have the property to bind to Akt2, reduce the kinase activity of Akt2 and increase the expression level in the diabetes mellitus morbid state are useful for the diagnosis of diabetes mellitus. In addition, the polypeptides, polynucleotides, expression vectors and cells of the present invention are useful for the screening of a substance which inhibits binding of the polypeptides of the present invention with Akt2 (namely a substance which reinforces function of Akt2). The substance selected by said screening is useful as a candidate substance for an insulin resistance improving agent and a diabetes mellitus improving agent.

Sequence Listing Free Text

An explanation of "Artificial Sequence" is described the numerical entry <223> of the following Sequence Listing. Illustratively, each of the nucleotide sequences represented by SEQ ID NOs:5 to 8 and 10 to 27 in the Sequence Listing is an artificially synthesized primer sequence. The nucleotide sequence represented by the sequence of SEQ ID NO:9 is a sequence consisting of the bases of from the 5183rd (5') to the 5162nd (3') positions of a cloning vector pACT2 (GenBank U29899).

In the foregoing, the invention has been described based on the specified embodiments, but changes and modifications obvious to those skilled in the art are included in the scope of the invention.

---

The invention claimed is:

1. An isolated polypeptide which comprises the amino acid sequence of SEQ ID NO:2 or SEQ ID NO:4 and which binds to Akt-homolog-2 ("Akt2").

2. An isolated polypeptide consisting of the amino acid sequence of SEQ ID NO:2 or SEQ ID NO:4.

3. An isolated polynucleotide encoding
   (1) a polypeptide which comprises the amino acid sequence of SEQ ID NO:2 and which binds to Akt-2,
   (2) a polypeptide which comprises the amino acid sequence of SEQ ID NO:4 and which binds to Akt-2,
   (3) a polypeptide consisting of the amino acid sequence of SEQ ID NO:2, or
   (4) a polypeptide consisting of the amino acid sequence of SEQ ID NO:4.

4. An expression vector comprising a polynucleotide encoding
   (1) a polypeptide which comprises the amino acid sequence of SEQ ID NO:2 and which binds to Akt-2,
   (2) a polypeptide which comprises the amino acid sequence of SEQ ID NO:4 and which binds to Akt-2,
   (3) a polypeptide consisting of the amino acid sequence of SEQ ID NO:2, or
   (4) a polypeptide consisting of the amino acid sequence of SEQ ID NO:4.

5. An isolated cell transformed with an expression vector comprising a polynucleotide encoding
   (1) a polypeptide which comprises the amino acid sequence of SEQ ID NO:2 and which binds to Akt-2,
   (2) a polypeptide which comprises the amino acid sequence of SEQ ID NO:4 and which binds to Akt-2,
   (3) a polypeptide consisting of the amino acid sequence of SEQ ID NO:2, or
   (4) a polypeptide consisting of the amino acid sequence of SEQ ID NO:4.

* * * * *

SEQUENCE LISTING

<160> NUMBER OF SEQ ID NOS: 27

<210> SEQ ID NO 1
<211> LENGTH: 1722
<212> TYPE: DNA
<213> ORGANISM: Mus sp.
<220> FEATURE:
<221> NAME/KEY: CDS
<222> LOCATION: (1)..(1719)

<400> SEQUENCE: 1

```
atg gca gct gtg ccg ccc ctg cgg gac cgc ttg agc ttc ttg cat agg        48
Met Ala Ala Val Pro Pro Leu Arg Asp Arg Leu Ser Phe Leu His Arg
1               5                   10                  15 ctc ccc atc ctg ttg aag ggg acc tca gat gat agc atc cca tgt cca        96
Leu Pro Ile Leu Leu Lys Gly Thr Ser Asp Asp Ser Ile Pro Cys Pro
            20                  25                  30 ggc tac ctg ttt gaa gag atc gcc aag att tcc cac gag tca cta ggc       144
Gly Tyr Leu Phe Glu Glu Ile Ala Lys Ile Ser His Glu Ser Leu Gly
        35                  40                  45 agc agc cag tgc ctg ctg gag tac ctc ctg aac cgt ctg gac agc agc       192
Ser Ser Gln Cys Leu Leu Glu Tyr Leu Leu Asn Arg Leu Asp Ser Ser
    50                  55                  60 tcc ggc cac gtg aag ctc aag gtg cta aag atc ttg ctt tac ctg tgt       240
Ser Gly His Val Lys Leu Lys Val Leu Lys Ile Leu Leu Tyr Leu Cys
65                  70                  75                  80 ggt cat ggc tct tcc tcc ttc ctc ctc atc ctc agg aga aac tct gct       288
Gly His Gly Ser Ser Ser Phe Leu Leu Ile Leu Arg Arg Asn Ser Ala
                85                  90                  95 ctc atc caa gaa gcc acg gct ttc tca ggg cct cca gat cct ctt cac       336
Leu Ile Gln Glu Ala Thr Ala Phe Ser Gly Pro Pro Asp Pro Leu His
            100                 105                 110 gga aat agc ttg tac cag aag gtg cgg gcg gct gcc cag gac ctg ggt       384
Gly Asn Ser Leu Tyr Gln Lys Val Arg Ala Ala Ala Gln Asp Leu Gly
        115                 120                 125 agc acc ctg ttc tca gat gcc gtg cca cag cct cca tcg cag cca cct       432
Ser Thr Leu Phe Ser Asp Ala Val Pro Gln Pro Pro Ser Gln Pro Pro
    130                 135                 140
```

-continued

| | |
|---|---|
| cag atc ccg cct ccc gca ggc atg ggc gcc cag gcc aga cct ctt agt<br>Gln Ile Pro Pro Pro Ala Gly Met Gly Ala Gln Ala Arg Pro Leu Ser<br>145                      150                      155                      160 | 480 |
| gcc ctg caa ggc ttc ggc tac acg aag gag agc agc cgg aca ggc tcc<br>Ala Leu Gln Gly Phe Gly Tyr Thr Lys Glu Ser Ser Arg Thr Gly Ser<br>                      165                      170                      175 | 528 |
| gca ggt gaa acc ttc ctc tcc acc atc cag agg gcc gca gag gta gtg<br>Ala Gly Glu Thr Phe Leu Ser Thr Ile Gln Arg Ala Ala Glu Val Val<br>                180                      185                      190 | 576 |
| gct aat gct gtg cgt cct gga cct gat aat cct tgt acc aag gga ccc<br>Ala Asn Ala Val Arg Pro Gly Pro Asp Asn Pro Cys Thr Lys Gly Pro<br>              195                      200                      205 | 624 |
| ttg ccg tat ggt gat tcc tac cag cct gca gtg aca cct tca gct agc<br>Leu Pro Tyr Gly Asp Ser Tyr Gln Pro Ala Val Thr Pro Ser Ala Ser<br>210                      215                      220 | 672 |
| cac aca cat ccc aac cct ggg aat cta ctc cct ggg gcc atc ctg ggg<br>His Thr His Pro Asn Pro Gly Asn Leu Leu Pro Gly Ala Ile Leu Gly<br>225                      230                      235                      240 | 720 |
| gcc aga gct gtg aga cac cag ccc ggg cag gct ggg ggc ggc tgg gat<br>Ala Arg Ala Val Arg His Gln Pro Gly Gln Ala Gly Gly Gly Trp Asp<br>                      245                      250                      255 | 768 |
| gag ctg gac agc agt cct agt tcc cag aat tcc tcc tgc acc agc aac<br>Glu Leu Asp Ser Ser Pro Ser Ser Gln Asn Ser Ser Cys Thr Ser Asn<br>                260                      265                      270 | 816 |
| ctg agc agg gcc tcg gac tcg ggc agt cgg tct ggc agt gac agc cac<br>Leu Ser Arg Ala Ser Asp Ser Gly Ser Arg Ser Gly Ser Asp Ser His<br>            275                      280                      285 | 864 |
| tct ggc acc agc cgg gag cca ggc gac ctg gca gaa agg gct gag gcc<br>Ser Gly Thr Ser Arg Glu Pro Gly Asp Leu Ala Glu Arg Ala Glu Ala<br>                      290                      295                      300 | 912 |
| acg ccc cca aat gac tgc cag caa gaa ctg aat cta gtg agg act gtg<br>Thr Pro Pro Asn Asp Cys Gln Gln Glu Leu Asn Leu Val Arg Thr Val<br>305                      310                      315                      320 | 960 |
| aca cag ggg cca cgt gtc ttc ctg agc cgt gag gag acg cag cac ttc<br>Thr Gln Gly Pro Arg Val Phe Leu Ser Arg Glu Glu Thr Gln His Phe<br>                      325                      330                      335 | 1008 |
| atc aaa gag tgt ggc ctg ctc aac tgt gag gca gtg ctg gag ctg ctc<br>Ile Lys Glu Cys Gly Leu Leu Asn Cys Glu Ala Val Leu Glu Leu Leu<br>                      340                      345                      350 | 1056 |
| ctg cgc cag ctg gtc ggg acc agt gag tgc gag cag atg agg gcg ctg<br>Leu Arg Gln Leu Val Gly Thr Ser Glu Cys Glu Gln Met Arg Ala Leu<br>            355                      360                      365 | 1104 |
| tgt gcc atc gcg tcc ttt ggg agt gct gac ctc ctg cct cag gag cac<br>Cys Ala Ile Ala Ser Phe Gly Ser Ala Asp Leu Leu Pro Gln Glu His<br>370                      375                      380 | 1152 |
| gtc ctc ctc ctg tgc cga cag cag ctg cag gaa ctt ggc gcg ggc agc<br>Val Leu Leu Leu Cys Arg Gln Gln Leu Gln Glu Leu Gly Ala Gly Ser<br>385                      390                      395                      400 | 1200 |
| cct gga cct gtg acc aac aaa gcc acc aag atc ctg aga cat ttt gaa<br>Pro Gly Pro Val Thr Asn Lys Ala Thr Lys Ile Leu Arg His Phe Glu<br>                      405                      410                      415 | 1248 |
| gcc tcc tgt gga caa cag ctc cct acc cta agg ctc tgt gcc cag ccc<br>Ala Ser Cys Gly Gln Gln Leu Pro Thr Leu Arg Leu Cys Ala Gln Pro<br>                      420                      425                      430 | 1296 |
| aac tct gca gct gcc cct gtg ggc cca gct gac ctg ctg acc agc ccc<br>Asn Ser Ala Ala Ala Pro Val Gly Pro Ala Asp Leu Leu Thr Ser Pro<br>                      435                      440                      445 | 1344 |
| gtg cct gcc cct ggg agc cag gtc tgc ctc cag cct ctc agc tcc gcc<br>Val Pro Ala Pro Gly Ser Gln Val Cys Leu Gln Pro Leu Ser Ser Ala<br>450                      455                      460 | 1392 |

```
aca gtg gta ccc agg agt cct gtg ctc ttt cca tcc ccc aat acc tta      1440
Thr Val Val Pro Arg Ser Pro Val Leu Phe Pro Ser Pro Asn Thr Leu
465                 470                 475                 480 cct ccg tct gct ctg gag gag ccc agc gag gtc cga acc caa ttg gtg      1488
Pro Pro Ser Ala Leu Glu Glu Pro Ser Glu Val Arg Thr Gln Leu Val
                485                 490                 495 tgt tct agt gaa cag ggg aca gaa tct gag cag agg ctg gag aac aca      1536
Cys Ser Ser Glu Gln Gly Thr Glu Ser Glu Gln Arg Leu Glu Asn Thr
            500                 505                 510 gac acc cca gag gat agc tcc agt ccg ctc ccg tgg agt ccc aac tct      1584
Asp Thr Pro Glu Asp Ser Ser Ser Pro Leu Pro Trp Ser Pro Asn Ser
        515                 520                 525 ttg ttt gct ggc atg gag ctg gtg gct tgc ccc cgc ctg cct tgc cac      1632
Leu Phe Ala Gly Met Glu Leu Val Ala Cys Pro Arg Leu Pro Cys His
    530                 535                 540 agc tcg cag gac ctc cag aca gat tta cag aag gtg acc aca gaa gct      1680
Ser Ser Gln Asp Leu Gln Thr Asp Leu Gln Lys Val Thr Thr Glu Ala
545                 550                 555                 560 ccg gtt tca gag cca tca gct ttt gca ttt tta aac atg tga              1722
Pro Val Ser Glu Pro Ser Ala Phe Ala Phe Leu Asn Met
                565                 570

<210> SEQ ID NO 2
<211> LENGTH: 573
<212> TYPE: PRT
<213> ORGANISM: Mus sp.

<400> SEQUENCE: 2

Met Ala Ala Val Pro Pro Leu Arg Asp Arg Leu Ser Phe Leu His Arg
1               5                   10                  15

Leu Pro Ile Leu Leu Lys Gly Thr Ser Asp Asp Ser Ile Pro Cys Pro
            20                  25                  30

Gly Tyr Leu Phe Glu Glu Ile Ala Lys Ile Ser His Glu Ser Leu Gly
        35                  40                  45

Ser Ser Gln Cys Leu Leu Glu Tyr Leu Leu Asn Arg Leu Asp Ser Ser
    50                  55                  60

Ser Gly His Val Lys Leu Lys Val Leu Lys Ile Leu Leu Tyr Leu Cys
65                  70                  75                  80

Gly His Gly Ser Ser Phe Leu Leu Ile Leu Arg Arg Asn Ser Ala
                85                  90                  95

Leu Ile Gln Glu Ala Thr Ala Phe Ser Gly Pro Pro Asp Pro Leu His
            100                 105                 110

Gly Asn Ser Leu Tyr Gln Lys Val Arg Ala Ala Gln Asp Leu Gly
        115                 120                 125

Ser Thr Leu Phe Ser Asp Ala Val Pro Gln Pro Ser Gln Pro Pro
130                 135                 140

Gln Ile Pro Pro Ala Gly Met Gly Ala Gln Ala Arg Pro Leu Ser
145                 150                 155                 160

Ala Leu Gln Gly Phe Gly Tyr Thr Lys Glu Ser Ser Arg Thr Gly Ser
                165                 170                 175

Ala Gly Glu Thr Phe Leu Ser Thr Ile Gln Arg Ala Ala Glu Val Val
            180                 185                 190

Ala Asn Ala Val Arg Pro Gly Pro Asp Asn Pro Cys Thr Lys Gly Pro
        195                 200                 205

Leu Pro Tyr Gly Asp Ser Tyr Gln Pro Ala Val Thr Pro Ser Ala Ser
    210                 215                 220
```

```
His Thr His Pro Asn Pro Gly Asn Leu Leu Pro Gly Ala Ile Leu Gly
225                 230                 235                 240

Ala Arg Ala Val Arg His Gln Pro Gly Gln Ala Gly Gly Gly Trp Asp
                245                 250                 255

Glu Leu Asp Ser Ser Pro Ser Ser Gln Asn Ser Ser Cys Thr Ser Asn
            260                 265                 270

Leu Ser Arg Ala Ser Asp Ser Gly Ser Arg Ser Gly Ser Asp Ser His
        275                 280                 285

Ser Gly Thr Ser Arg Glu Pro Gly Asp Leu Ala Glu Arg Ala Glu Ala
    290                 295                 300

Thr Pro Pro Asn Asp Cys Gln Gln Glu Leu Asn Leu Val Arg Thr Val
305                 310                 315                 320

Thr Gln Gly Pro Arg Val Phe Leu Ser Arg Glu Glu Thr Gln His Phe
                325                 330                 335

Ile Lys Glu Cys Gly Leu Leu Asn Cys Glu Ala Val Leu Glu Leu Leu
            340                 345                 350

Leu Arg Gln Leu Val Gly Thr Ser Glu Cys Glu Gln Met Arg Ala Leu
        355                 360                 365

Cys Ala Ile Ala Ser Phe Gly Ser Ala Asp Leu Leu Pro Gln Glu His
    370                 375                 380

Val Leu Leu Cys Arg Gln Gln Leu Gln Glu Leu Gly Ala Gly Ser
385                 390                 395                 400

Pro Gly Pro Val Thr Asn Lys Ala Thr Lys Ile Leu Arg His Phe Glu
                405                 410                 415

Ala Ser Cys Gly Gln Gln Leu Pro Thr Leu Arg Leu Cys Ala Gln Pro
            420                 425                 430

Asn Ser Ala Ala Ala Pro Val Gly Pro Ala Asp Leu Leu Thr Ser Pro
        435                 440                 445

Val Pro Ala Pro Gly Ser Gln Val Cys Leu Gln Pro Leu Ser Ser Ala
    450                 455                 460

Thr Val Val Pro Arg Ser Pro Val Leu Phe Pro Ser Pro Asn Thr Leu
465                 470                 475                 480

Pro Pro Ser Ala Leu Glu Glu Pro Ser Glu Val Arg Thr Gln Leu Val
                485                 490                 495

Cys Ser Ser Glu Gln Gly Thr Glu Ser Glu Gln Arg Leu Glu Asn Thr
            500                 505                 510

Asp Thr Pro Glu Asp Ser Ser Pro Leu Pro Trp Ser Pro Asn Ser
        515                 520                 525

Leu Phe Ala Gly Met Glu Leu Val Ala Cys Pro Arg Leu Pro Cys His
    530                 535                 540

Ser Ser Gln Asp Leu Gln Thr Asp Leu Gln Lys Val Thr Thr Glu Ala
545                 550                 555                 560

Pro Val Ser Glu Pro Ser Ala Phe Ala Phe Leu Asn Met
                565                 570

<210> SEQ ID NO 3
<211> LENGTH: 1782
<212> TYPE: DNA
<213> ORGANISM: Homo sapiens
<220> FEATURE:
<221> NAME/KEY: CDS
<222> LOCATION: (1)..(1782)

<400> SEQUENCE: 3 atg gct gcc gcg ccg ccg cta cgg gac cgc ctg agc ttt cta cac cgg     48
Met Ala Ala Ala Pro Pro Leu Arg Asp Arg Leu Ser Phe Leu His Arg
```

-continued

```
1               5                   10                  15 ctc ccg att ctc ctg aag ggg acg tcc gat gat gat gtc ccg tgt ccg      96
Leu Pro Ile Leu Leu Lys Gly Thr Ser Asp Asp Asp Val Pro Cys Pro
            20                  25                  30 ggc tac ctg ttt gaa gag att gct aaa atc tcc cac gag tct ccg ggc     144
Gly Tyr Leu Phe Glu Glu Ile Ala Lys Ile Ser His Glu Ser Pro Gly
        35                  40                  45 agc agc cag tgc ctg ctg gag tac ctc ctg agc cgc ctg cac agc agc     192
Ser Ser Gln Cys Leu Leu Glu Tyr Leu Leu Ser Arg Leu His Ser Ser
    50                  55                  60 tcc ggc cac ggg aag ctc aag gtg ctg aag atc ctg ctc tat ctg tgc     240
Ser Gly His Gly Lys Leu Lys Val Leu Lys Ile Leu Leu Tyr Leu Cys
65                  70                  75                  80 agc cac ggc tcc tcc ttc ttc ctc atc ctc aaa cgc aac tct gcc         288
Ser His Gly Ser Ser Phe Phe Leu Leu Ile Leu Lys Arg Asn Ser Ala
                85                  90                  95 ttc atc cag gaa gct gca gct ttt gca ggg ccc cca gat cct ctg cac     336
Phe Ile Gln Glu Ala Ala Ala Phe Ala Gly Pro Pro Asp Pro Leu His
            100                 105                 110 ggg aac agc ttg tac cag aag gtt cgc gcg gcc gcg cag gac ttg ggg     384
Gly Asn Ser Leu Tyr Gln Lys Val Arg Ala Ala Ala Gln Asp Leu Gly
        115                 120                 125 agc acc ctg ttc tcg gac acc gtg ttg ccg ctg gct ccc tcc cag cct     432
Ser Thr Leu Phe Ser Asp Thr Val Leu Pro Leu Ala Pro Ser Gln Pro
    130                 135                 140 ctg ggg acc ccg cct gcc aca ggc atg ggc tcc cag gcc agg ccg cac     480
Leu Gly Thr Pro Pro Ala Thr Gly Met Gly Ser Gln Ala Arg Pro His
145                 150                 155                 160 agc acc ctc cag ggt ttc ggc tac agc aag gaa cac ggc cgc acg ggc     528
Ser Thr Leu Gln Gly Phe Gly Tyr Ser Lys Glu His Gly Arg Thr Gly
                165                 170                 175 tcg gca ggc gaa gcc ttc ctc tcc acc atc cag aag gcc gca gag gtg     576
Ser Ala Gly Glu Ala Phe Leu Ser Thr Ile Gln Lys Ala Ala Glu Val
            180                 185                 190 gtg gcc agc gcc atg cgc ccc ggg ccc gag agt ccc agt acc cgg agg     624
Val Ala Ser Ala Met Arg Pro Gly Pro Glu Ser Pro Ser Thr Arg Arg
        195                 200                 205 ctc ctg ccg cgg ggt gac acc tac cag cct gcc atg atg cct tca gcc     672
Leu Leu Pro Arg Gly Asp Thr Tyr Gln Pro Ala Met Met Pro Ser Ala
    210                 215                 220 agc cac ggt ccc cca acc ctg ggg aac cta ctc ccc ggg gcc att cca     720
Ser His Gly Pro Pro Thr Leu Gly Asn Leu Leu Pro Gly Ala Ile Pro
225                 230                 235                 240 ggt ccc cga gct gtg agg cat cag cct ggg cag gcc gga ggg ggc tgg     768
Gly Pro Arg Ala Val Arg His Gln Pro Gly Gln Ala Gly Gly Gly Trp
                245                 250                 255 gat gag ctg gac agc ggc ccc agc tct cag aat tcc tcc cag aac agc     816
Asp Glu Leu Asp Ser Gly Pro Ser Ser Gln Asn Ser Ser Gln Asn Ser
            260                 265                 270 gac ctg agc agg gtc tcg gac tcg ggc agt cat tcc ggc agc gac agc     864
Asp Leu Ser Arg Val Ser Asp Ser Gly Ser His Ser Gly Ser Asp Ser
        275                 280                 285 cat tca ggg gcc agc cgg gag ccg ggt gac ctg gca gaa agg gtc gag     912
His Ser Gly Ala Ser Arg Glu Pro Gly Asp Leu Ala Glu Arg Val Glu
    290                 295                 300 gtg gtg gcc ctg agt gac tgt cag cag gag ttg agc ttg gtg agg act     960
Val Val Ala Leu Ser Asp Cys Gln Gln Glu Leu Ser Leu Val Arg Thr
305                 310                 315                 320 gtg act cgg gga cca cgc gcc ttc ctg agc cgc gag gag gca cag cac    1008
```

```
ttc atc aaa gcg tgt gga ctg ctc aac tgt gag gcc gtg ctg cag ctg    1056
Phe Ile Lys Ala Cys Gly Leu Leu Asn Cys Glu Ala Val Leu Gln Leu
        340                 345                 350 ctg acc tgc cac ctg cgt ggg acc agt gaa tgc acg cag ctg agg gcg    1104
Leu Thr Cys His Leu Arg Gly Thr Ser Glu Cys Thr Gln Leu Arg Ala
    355                 360                 365 ctg tgt gcc atc gcc tcc ctg ggg agc agc gac ctc ctc ccc cag gag    1152
Leu Cys Ala Ile Ala Ser Leu Gly Ser Ser Asp Leu Leu Pro Gln Glu
370                 375                 380 cac atc ctc ctc cgc acc cgg ccg tgg ctg cag gag ctc agc atg ggc    1200
His Ile Leu Leu Arg Thr Arg Pro Trp Leu Gln Glu Leu Ser Met Gly
385                 390                 395                 400 agc ccg gga cct gtg acc aac aag gcc acc aag atc ctg agg cac ttt    1248
Ser Pro Gly Pro Val Thr Asn Lys Ala Thr Lys Ile Leu Arg His Phe
                405                 410                 415 gag gcc tcc tgt ggg cag ctg tcc cct gcc cgg ggc acc tca gct gag    1296
Glu Ala Ser Cys Gly Gln Leu Ser Pro Ala Arg Gly Thr Ser Ala Glu
            420                 425                 430 cct ggc ccc aca gcc gcc ctc cca ggc cca tct gac ctg ctg acc gac    1344
Pro Gly Pro Thr Ala Ala Leu Pro Gly Pro Ser Asp Leu Leu Thr Asp
        435                 440                 445 gct gtg cct ctc cct ggg agc cag gtc ttc ctg cag cct ctg agt tca    1392
Ala Val Pro Leu Pro Gly Ser Gln Val Phe Leu Gln Pro Leu Ser Ser
    450                 455                 460 acc ccg gtc tcg tcc cgg agc cct gct ccc tca tct ggg atg ccg tcc    1440
Thr Pro Val Ser Ser Arg Ser Pro Ala Pro Ser Ser Gly Met Pro Ser
465                 470                 475                 480 agc cct gtg ccc acc cca ccc cca gat gcc tcc ccc att cca gcc ccc    1488
Ser Pro Val Pro Thr Pro Pro Pro Asp Ala Ser Pro Ile Pro Ala Pro
                485                 490                 495 gga gac ccc agc gag gcc gag gcc aga ctg gca gaa agc agg cgg tgg    1536
Gly Asp Pro Ser Glu Ala Glu Ala Arg Leu Ala Glu Ser Arg Arg Trp
            500                 505                 510 aga cct gaa cgg atc ccg ggg ggc acg gac agc cca aag aga ggc ccc    1584
Arg Pro Glu Arg Ile Pro Gly Gly Thr Asp Ser Pro Lys Arg Gly Pro
        515                 520                 525 agc agc tgt gcg tgg agc cgc gac tcc ttg ttt gct ggc atg gag ctg    1632
Ser Ser Cys Ala Trp Ser Arg Asp Ser Leu Phe Ala Gly Met Glu Leu
    530                 535                 540 gtg gcc tgt ccc cgc ctg gtg ggg gct ggg gct gct gcg gga gag tcc    1680
Val Ala Cys Pro Arg Leu Val Gly Ala Gly Ala Ala Ala Gly Glu Ser
545                 550                 555                 560 tgt cct gat gct ccc cgc gcc ccc caa aca tcg tcc cag agg aca gca    1728
Cys Pro Asp Ala Pro Arg Ala Pro Gln Thr Ser Ser Gln Arg Thr Ala
                565                 570                 575 gcc aaa gag cct cct ggc tca gag ccg tca gct ttc gcg ttc ctg aac    1776
Ala Lys Glu Pro Pro Gly Ser Glu Pro Ser Ala Phe Ala Phe Leu Asn
            580                 585                 590 gcc tga                                                            1782
Ala
```

<210> SEQ ID NO 4
<211> LENGTH: 593
<212> TYPE: PRT
<213> ORGANISM: Homo sapiens

<400> SEQUENCE: 4

Met Ala Ala Ala Pro Pro Leu Arg Asp Arg Leu Ser Phe Leu His Arg

```
1               5                   10                  15
Leu Pro Ile Leu Leu Lys Gly Thr Ser Asp Asp Val Pro Cys Pro
            20                  25                  30

Gly Tyr Leu Phe Glu Glu Ile Ala Lys Ile Ser His Glu Ser Pro Gly
            35                  40                  45

Ser Ser Gln Cys Leu Leu Glu Tyr Leu Leu Ser Arg Leu His Ser Ser
            50                  55                  60

Ser Gly His Gly Lys Leu Lys Val Leu Lys Ile Leu Leu Tyr Leu Cys
65                      70                  75                  80

Ser His Gly Ser Ser Phe Phe Leu Leu Ile Leu Lys Arg Asn Ser Ala
                85                  90                  95

Phe Ile Gln Glu Ala Ala Ala Phe Ala Gly Pro Pro Asp Pro Leu His
            100                 105                 110

Gly Asn Ser Leu Tyr Gln Lys Val Arg Ala Ala Gln Asp Leu Gly
            115                 120                 125

Ser Thr Leu Phe Ser Asp Thr Val Leu Pro Leu Ala Pro Ser Gln Pro
            130                 135                 140

Leu Gly Thr Pro Pro Ala Thr Gly Met Gly Ser Gln Ala Arg Pro His
145                 150                 155                 160

Ser Thr Leu Gln Gly Phe Gly Tyr Ser Lys Glu His Gly Arg Thr Gly
            165                 170                 175

Ser Ala Gly Glu Ala Phe Leu Ser Thr Ile Gln Lys Ala Ala Glu Val
            180                 185                 190

Val Ala Ser Ala Met Arg Pro Gly Pro Glu Ser Pro Ser Thr Arg Arg
            195                 200                 205

Leu Leu Pro Arg Gly Asp Thr Tyr Gln Pro Ala Met Met Pro Ser Ala
            210                 215                 220

Ser His Gly Pro Pro Thr Leu Gly Asn Leu Leu Pro Gly Ala Ile Pro
225                 230                 235                 240

Gly Pro Arg Ala Val Arg His Gln Pro Gly Gln Ala Gly Gly Gly Trp
            245                 250                 255

Asp Glu Leu Asp Ser Gly Pro Ser Ser Gln Asn Ser Ser Gln Asn Ser
            260                 265                 270

Asp Leu Ser Arg Val Ser Asp Ser Gly Ser His Ser Gly Ser Asp Ser
            275                 280                 285

His Ser Gly Ala Ser Arg Glu Pro Gly Asp Leu Ala Glu Arg Val Glu
            290                 295                 300

Val Val Ala Leu Ser Asp Cys Gln Gln Glu Leu Ser Leu Val Arg Thr
305                 310                 315                 320

Val Thr Arg Gly Pro Arg Ala Phe Leu Ser Arg Glu Glu Ala Gln His
            325                 330                 335

Phe Ile Lys Ala Cys Gly Leu Leu Asn Cys Glu Ala Val Leu Gln Leu
            340                 345                 350

Leu Thr Cys His Leu Arg Gly Thr Ser Glu Cys Thr Gln Leu Arg Ala
            355                 360                 365

Leu Cys Ala Ile Ala Ser Leu Gly Ser Ser Asp Leu Leu Pro Gln Glu
            370                 375                 380

His Ile Leu Leu Arg Thr Arg Pro Trp Leu Gln Glu Leu Ser Met Gly
385                 390                 395                 400

Ser Pro Gly Pro Val Thr Asn Lys Ala Thr Lys Ile Leu Arg His Phe
            405                 410                 415

Glu Ala Ser Cys Gly Gln Leu Ser Pro Ala Arg Gly Thr Ser Ala Glu
            420                 425                 430
```

```
Pro Gly Pro Thr Ala Ala Leu Pro Gly Pro Ser Asp Leu Leu Thr Asp
        435                 440                 445

Ala Val Pro Leu Pro Gly Ser Gln Val Phe Leu Gln Pro Leu Ser Ser
    450                 455                 460

Thr Pro Val Ser Ser Arg Ser Pro Ala Pro Ser Ser Gly Met Pro Ser
465                 470                 475                 480

Ser Pro Val Pro Thr Pro Pro Asp Ala Ser Pro Ile Pro Ala Pro
                485                 490                 495

Gly Asp Pro Ser Glu Ala Glu Ala Arg Leu Ala Glu Ser Arg Arg Trp
            500                 505                 510

Arg Pro Glu Arg Ile Pro Gly Gly Thr Asp Ser Pro Lys Arg Gly Pro
        515                 520                 525

Ser Ser Cys Ala Trp Ser Arg Asp Ser Leu Phe Ala Gly Met Glu Leu
    530                 535                 540

Val Ala Cys Pro Arg Leu Val Gly Ala Gly Ala Ala Gly Glu Ser
545                 550                 555                 560

Cys Pro Asp Ala Pro Arg Ala Pro Gln Thr Ser Ser Gln Arg Thr Ala
                565                 570                 575

Ala Lys Glu Pro Pro Gly Ser Glu Pro Ser Ala Phe Ala Phe Leu Asn
            580                 585                 590

Ala

<210> SEQ ID NO 5
<211> LENGTH: 27
<212> TYPE: DNA
<213> ORGANISM: Artificial Sequence
<220> FEATURE:
<223> OTHER INFORMATION: Chemically-synthesized primer sequence

<400> SEQUENCE: 5
cgtaccacgc tgccaccatg aatgagg                               27

<210> SEQ ID NO 6
<211> LENGTH: 27
<212> TYPE: DNA
<213> ORGANISM: Artificial Sequence
<220> FEATURE:
<223> OTHER INFORMATION: Chemically-synthesized primer sequence

<400> SEQUENCE: 6
gcagcgagcg tgcgtcctct gcgtggg                               27

<210> SEQ ID NO 7
<211> LENGTH: 61
<212> TYPE: DNA
<213> ORGANISM: Artificial Sequence
<220> FEATURE:
<223> OTHER INFORMATION: Chemically-synthesized primer sequence

<400> SEQUENCE: 7
agagagtagt aacaaaggtc aaagacagtt gactgtatcg atgaatgagg tgtctgtcat    60
c                                                                   61

<210> SEQ ID NO 8
<211> LENGTH: 58
<212> TYPE: DNA
<213> ORGANISM: Artificial Sequence
<220> FEATURE:
<223> OTHER INFORMATION: Chemically-synthesized primer sequence
```

```
<400> SEQUENCE: 8
tggagacttg accaaacctc tggcgaagaa gtccaaagct tcactcgcgg atgctggc    58

<210> SEQ ID NO 9
<211> LENGTH: 22
<212> TYPE: DNA
<213> ORGANISM: Artificial Sequence
<220> FEATURE:
<223> OTHER INFORMATION: Sequence containing nucleotides 5183-5162 of
      cloning vector pACT2 (GenBank U29899)

<400> SEQUENCE: 9
cgcgtttgga atcactacag gg                                           22

<210> SEQ ID NO 10
<211> LENGTH: 24
<212> TYPE: DNA
<213> ORGANISM: Artificial Sequence
<220> FEATURE:
<223> OTHER INFORMATION: Chemically-synthesized primer sequence

<400> SEQUENCE: 10
cagttgagca ggccacactc tttg                                         24

<210> SEQ ID NO 11
<211> LENGTH: 20
<212> TYPE: DNA
<213> ORGANISM: Artificial Sequence
<220> FEATURE:
<223> OTHER INFORMATION: Chemically-synthesized primer sequence

<400> SEQUENCE: 11
taatacgact cactataggg                                              20

<210> SEQ ID NO 12
<211> LENGTH: 18
<212> TYPE: DNA
<213> ORGANISM: Artificial Sequence
<220> FEATURE:
<223> OTHER INFORMATION: Chemically-synthesized primer sequence

<400> SEQUENCE: 12
atggcagctg tgccgccc                                                18

<210> SEQ ID NO 13
<211> LENGTH: 21
<212> TYPE: DNA
<213> ORGANISM: Artificial Sequence
<220> FEATURE:
<223> OTHER INFORMATION: Chemically-synthesized primer sequence

<400> SEQUENCE: 13
catgtttaaa aatgcaaaag c                                            21

<210> SEQ ID NO 14
<211> LENGTH: 22
<212> TYPE: DNA
<213> ORGANISM: Artificial Sequence
<220> FEATURE:
<223> OTHER INFORMATION: Chemically-synthesized primer sequence

<400> SEQUENCE: 14
catgtccagg ctacctgttt ga                                           22

<210> SEQ ID NO 15
```

```
<211> LENGTH: 17
<212> TYPE: DNA
<213> ORGANISM: Artificial Sequence
<220> FEATURE:
<223> OTHER INFORMATION: Chemically-synthesized primer sequence

<400> SEQUENCE: 15
caggcactgg ctgctgc                                                     17

<210> SEQ ID NO 16
<211> LENGTH: 20
<212> TYPE: DNA
<213> ORGANISM: Artificial Sequence
<220> FEATURE:
<223> OTHER INFORMATION: Chemically-synthesized primer sequence

<400> SEQUENCE: 16
aaagtggaga ttgttgccat                                                  20

<210> SEQ ID NO 17
<211> LENGTH: 19
<212> TYPE: DNA
<213> ORGANISM: Artificial Sequence
<220> FEATURE:
<223> OTHER INFORMATION: Chemically-synthesized primer sequence

<400> SEQUENCE: 17
ttgactgtgc cgttgaatt                                                   19

<210> SEQ ID NO 18
<211> LENGTH: 17
<212> TYPE: DNA
<213> ORGANISM: Artificial Sequence
<220> FEATURE:
<223> OTHER INFORMATION: Chemically-synthesized primer sequence

<400> SEQUENCE: 18
atggctgccg cgccgcc                                                     17

<210> SEQ ID NO 19
<211> LENGTH: 20
<212> TYPE: DNA
<213> ORGANISM: Artificial Sequence
<220> FEATURE:
<223> OTHER INFORMATION: Chemically-synthesized primer sequence

<400> SEQUENCE: 19
ggcgttcagg aacgcgaaag                                                  20

<210> SEQ ID NO 20
<211> LENGTH: 18
<212> TYPE: DNA
<213> ORGANISM: Artificial Sequence
<220> FEATURE:
<223> OTHER INFORMATION: Chemically-synthesized primer sequence

<400> SEQUENCE: 20
gactgtgact cggggacc                                                    18

<210> SEQ ID NO 21
<211> LENGTH: 21
<212> TYPE: DNA
<213> ORGANISM: Artificial Sequence
<220> FEATURE:
<223> OTHER INFORMATION: Chemically-synthesized primer sequence

<400> SEQUENCE: 21
```

```
gatccccggg tatcgcatcc a                                              21

<210> SEQ ID NO 22
<211> LENGTH: 21
<212> TYPE: DNA
<213> ORGANISM: Artificial Sequence
<220> FEATURE:
<223> OTHER INFORMATION: Chemically-synthesized primer sequence

<400> SEQUENCE: 22
agcttggatg cgatacccgg g                                              21

<210> SEQ ID NO 23
<211> LENGTH: 19
<212> TYPE: DNA
<213> ORGANISM: Artificial Sequence
<220> FEATURE:
<223> OTHER INFORMATION: Chemically-synthesized primer sequence

<400> SEQUENCE: 23
tttgcagggc tggcaagcc                                                 19

<210> SEQ ID NO 24
<211> LENGTH: 39
<212> TYPE: DNA
<213> ORGANISM: Artificial Sequence
<220> FEATURE:
<223> OTHER INFORMATION: Chemically-synthesized primer sequence

<400> SEQUENCE: 24
aattcggaag gccaagaact tcatcgttcg cagagggtc                           39

<210> SEQ ID NO 25
<211> LENGTH: 38
<212> TYPE: DNA
<213> ORGANISM: Artificial Sequence
<220> FEATURE:
<223> OTHER INFORMATION: Chemically-synthesized primer sequence

<400> SEQUENCE: 25
tcgagaccct ctgcgaacga tgaagttctt ggccttcc                            38

<210> SEQ ID NO 26
<211> LENGTH: 30
<212> TYPE: DNA
<213> ORGANISM: Artificial Sequence
<220> FEATURE:
<223> OTHER INFORMATION: Chemically-synthesized primer sequence

<400> SEQUENCE: 26
gggactacaa ggacgatgac gataagtagc                                     30

<210> SEQ ID NO 27
<211> LENGTH: 36
<212> TYPE: DNA
<213> ORGANISM: Artificial Sequence
<220> FEATURE:
<223> OTHER INFORMATION: Chemically-synthesized primer sequence

<400> SEQUENCE: 27
ggccgctact tatcgtcatc gtccttgtag tcccgc                              36
```